United States Patent
Bryans et al.

(10) Patent No.: US 7,449,462 B2
(45) Date of Patent: Nov. 11, 2008

(54) TRIAZOLE DERIVATIVES WHICH INHIBIT VASOPRESSIN ANTAGONISTIC ACTIVITY

(75) Inventors: Justin S. Bryans, Canterbury (GB); Patrick S. Johnson, Sandwich (GB); Thomas Ryckmans, Sandwich (GB); Alan Stobie, Sandwich (GB)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/588,876

(22) PCT Filed: Jan. 11, 2005

(86) PCT No.: PCT/IB2005/000079

§ 371 (c)(1), (2), (4) Date: Jan. 29, 2007

(87) PCT Pub. No.: WO2005/079808

PCT Pub. Date: Sep. 1, 2005

(65) Prior Publication Data

US 2007/0203132 A1 Aug. 30, 2007

Related U.S. Application Data

(60) Provisional application No. 60/549,407, filed on Mar. 1, 2004.

(30) Foreign Application Priority Data

Jan. 22, 2004 (GB) .................................. 0401384.3

(51) Int. Cl.
*C07D 401/14* (2006.01)
*A61K 31/5517* (2006.01)

(52) U.S. Cl. ............... 514/235.8; 514/275; 514/318; 514/326; 544/122; 544/331; 546/210

(58) Field of Classification Search ................ 544/122, 544/331; 546/210; 514/235.8, 275, 318, 514/326
See application file for complete search history.

(56) References Cited

U.S. PATENT DOCUMENTS

| 3,840,597 | A | 10/1974 | Moore et al. ............. 260/556 F |
| 4,233,299 | A | 11/1980 | Trummlitz et al. .......... 424/246 |
| 4,881,460 | A | 11/1989 | Bannister et al. ............. 101/91 |
| 4,885,367 | A | 12/1989 | Yoshikawa et al. .......... 546/216 |
| 5,134,127 | A | 7/1992 | Rajewski et al. .............. 514/58 |
| 5,344,991 | A | 9/1994 | Reitz et al. ..................... 568/34 |
| 5,380,738 | A | 1/1995 | Talley et al. ................ 548/235 |
| 5,418,254 | A | 5/1995 | Huang et al. ................ 549/342 |
| 5,466,823 | A | 11/1995 | Talley et al. ................ 546/279 |
| 5,474,995 | A | 12/1995 | Ducharme et al. .......... 514/241 |
| 5,475,018 | A | 12/1995 | Bertenshaw et al. ..... 548/377.1 |
| 5,482,941 | A | 1/1996 | Terrett et al. ................ 544/284 |
| 5,486,534 | A | 1/1996 | Penning et al. .......... 548/375.1 |
| 5,521,207 | A | 5/1996 | Graneto ..................... 514/406 |
| 5,547,975 | A | 8/1996 | Graneto et al. ........... 548/359.5 |
| 5,576,322 | A | 11/1996 | Kimura et al. ............... 514/259 |
| 5,591,742 | A | 1/1997 | Terrett et al. ................ 544/119 |
| 5,596,008 | A | 1/1997 | Lee ............................ 546/339 |
| 5,616,601 | A | 4/1997 | Khanna et al. .............. 546/184 |
| 5,620,999 | A | 4/1997 | Barta et al. ............... 548/334.5 |
| 5,633,272 | A | 5/1997 | Talley et al. ................ 514/378 |
| 5,643,933 | A | 7/1997 | Graneto et al. ............. 514/378 |
| 5,668,161 | A | 9/1997 | Collins et al. ............... 548/194 |
| 5,670,510 | A | 9/1997 | Huang et al. |

(Continued)

FOREIGN PATENT DOCUMENTS

EP 0463756 6/1991

(Continued)

OTHER PUBLICATIONS

Carter, J., et al. *Expert Opinion on Therapeutic Patents*, "Recently reported inhibitors of cyclooxygenase-2", vol. 8(1), pp. 21-29 (1997).

(Continued)

*Primary Examiner*—Deepak Rao
(74) *Attorney, Agent, or Firm*—Gregg C. Benson; John A. Wichtowski

(57) ABSTRACT

Compounds of formula (I),

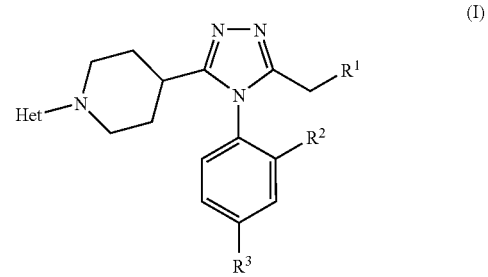

or pharmaceutically acceptable derivatives thereof, wherein:
Het represents 2-pyridinyl or 2-pyrimidinyl;
$R^1$ represents H, $C_{1-3}$ alkyl or a nitrogen-containing heterocyclic ring having 5 or 6 ring atoms;
$R^2$ represents H, benzyl or $C_{1-3}$ alkyl; and
$R^3$ represents H, methyl, methoxy or chloro;
are useful for treating anxiety, cardiovascular disease (including angina, atherosclerosis, hypertension, heart failure, edema, hypernatremia), dysmenorrhoea (primary and secondary), endometriosis, emesis (motion sickness), intrauterine growth retardation, inflammation (including rheumatoid arthritis), mittlesmerchz, preclampsia, premature ejaculation, premature (preterm) labor and Raynaud's disease.

13 Claims, No Drawings

U.S. PATENT DOCUMENTS

| | | | | |
|---|---|---|---|---|
| 5,731,343 | A | 3/1998 | Feng et al. | 514/450 |
| 5,734,053 | A | 3/1998 | Terrett et al. | 544/277 |
| 5,739,166 | A | 4/1998 | Li et al. | 514/716 |
| 5,861,419 | A | 1/1999 | Fortin et al. | 514/356 |
| 5,932,598 | A | 8/1999 | Talley et al. | 514/341 |
| 5,945,539 | A | 8/1999 | Haruta et al. | 548/235 |
| 5,968,974 | A | 10/1999 | Kargman et al. | 514/461 |
| 5,981,576 | A | 11/1999 | Belley et al. | 514/473 |
| 5,994,379 | A | 11/1999 | Bayly et al. | 514/367 |
| 5,994,381 | A | 11/1999 | Haruta et al. | 514/374 |
| 6,001,843 | A | 12/1999 | Dube et al. | 514/277 |
| 6,002,014 | A | 12/1999 | Haruta et al. | 548/235 |
| 6,004,948 | A | 12/1999 | Blaschke et al. | 514/155 |
| 6,020,343 | A | 2/2000 | Belley et al. | 514/309 |
| 6,028,202 | A | 2/2000 | Connolly et al. | 548/376.1 |
| 6,034,256 | A | 3/2000 | Carter et al. | 549/456 |
| 6,040,320 | A | 3/2000 | Beers et al. | 514/341 |
| 6,040,450 | A | 3/2000 | Davies et al. | 546/256 |
| 6,043,252 | A | 3/2000 | Bombrun et al. | 514/292 |
| 6,046,217 | A | 4/2000 | Friesen et al. | 514/347 |
| 6,046,236 | A | 4/2000 | Hamanaka et al. | 514/535 |
| 6,057,319 | A | 5/2000 | Black et al. | 514/242 |
| 6,071,936 | A | 6/2000 | Dube et al. | 514/334 |
| 6,077,850 | A | 6/2000 | Carter et al. | 514/311 |
| 6,077,868 | A | 6/2000 | Cook et al. | 514/560 |
| 6,077,869 | A | 6/2000 | Sui et al. | 514/615 |
| 6,080,876 | A | 6/2000 | Dorziotis et al. | 549/319 |
| 6,083,969 | A | 7/2000 | Ferro et al. | 514/403 |
| 6,127,545 | A | 10/2000 | Pye et al. | 546/286 |
| 6,130,334 | A | 10/2000 | Pye et al. | 546/286 |
| 6,133,292 | A | 10/2000 | Wang et al. | 514/336 |
| 6,136,831 | A | 10/2000 | Aotsuka et al. | 514/367 |
| 6,140,515 | A | 10/2000 | Chen et al. | 549/324 |
| 6,143,746 | A | 11/2000 | Daugan et al. | 514/249 |
| 6,143,747 | A | 11/2000 | Freskos et al. | 514/253.11 |
| 6,153,787 | A | 11/2000 | Rossen et al. | 560/187 |
| 6,169,188 | B1 | 1/2001 | Belley et al. | 549/330 |
| 6,180,651 | B1 | 1/2001 | Nicolai et al. | 514/336 |
| 6,204,387 | B1 | 3/2001 | Davies et al. | 546/315 |
| 6,222,048 | B1 | 4/2001 | Black et al. | 549/60 |
| 6,239,137 | B1 | 5/2001 | Karmali et al. | 514/274 |
| 6,239,173 | B1 | 5/2001 | Wang et al. | 514/473 |
| 6,251,904 | B1 | 6/2001 | Bunnage et al. | 514/252.6 |
| 6,271,253 | B1 | 8/2001 | Carter et al. | 514/432 |
| 6,274,590 | B1 | 8/2001 | Penning et al. | 514/438 |
| 6,297,282 | B1 | 10/2001 | Hartmann et al. | 514/603 |
| 6,300,363 | B1 | 10/2001 | Stevens et al. | 514/415 |
| 6,303,628 | B1 | 10/2001 | Nakao et al. | 514/307 |
| 6,306,890 | B1 | 10/2001 | Kalgutkar et al. | 514/419 |
| 6,307,047 | B1 | 10/2001 | Black et al. | 544/240 |
| 6,310,079 | B1 | 10/2001 | Okumura et al. | 514/338 |
| 6,329,421 | B1 | 12/2001 | Prasit et al. | 514/443 |
| 6,333,330 | B1 | 12/2001 | Bunnage et al. | 514/258 |
| 6,340,694 | B1 | 1/2002 | Joo et al. | 514/337 |
| 6,359,182 | B1 | 3/2002 | Stamler et al. | 568/949 |
| 6,362,178 | B1 | 3/2002 | Shenke et al. | 544/184 |
| 6,362,209 | B1 | 3/2002 | Haruta et al. | 514/374 |
| 6,369,275 | B1 | 4/2002 | Davies et al. | 568/56 |
| 6,376,519 | B1 | 4/2002 | Reddy et al. | 514/341 |
| 6,395,724 | B1 | 5/2002 | Judice et al. | 514/183 |
| 6,420,557 | B1 | 7/2002 | Storey et al. | 544/262 |
| 6,432,999 | B2 | 8/2002 | Lu et al. | 548/375.1 |
| 6,462,047 | B1 | 10/2002 | Bombrun et al. | 546/85 |
| 6,583,147 | B1 | 6/2003 | Kyun et al. | 514/262.1 |
| 6,723,719 | B1 | 4/2004 | Bunnage et al. | 514/241 |
| 6,756,373 | B1 | 6/2004 | Allerton et al. | 546/276.1 |
| 6,770,645 | B2 | 8/2004 | Newman et al. | 514/263.22 |
| 6,784,185 | B2 | 8/2004 | Allerton et al. | 514/262.1 |
| 6,794,387 | B2 | 9/2004 | Allerton et al. | 514/243 |
| 6,825,197 | B2 | 11/2004 | Sawyer et al. | 544/343 |
| 6,838,456 | B2 | 1/2005 | Gosmini et al. | 546/64 |
| 6,858,620 | B2 | 2/2005 | Shultze et al. | 514/285 |
| 6,872,721 | B2 | 3/2005 | Sawyer et al. | 514/250 |
| 6,878,711 | B2 | 4/2005 | Shultze et al. | 544/9 |
| 6,903,099 | B2 | 6/2005 | Shultze et al. | 544/343 |
| 6,911,542 | B2 | 6/2005 | Shultze et al. | 544/343 |
| 6,960,587 | B2 | 11/2005 | Shultze et al. | 544/345 |
| 6,962,918 | B2 | 11/2005 | Shultze et al. | 544/343 |
| 6,984,641 | B2 | 1/2006 | Gellibert et al. | 514/285 |
| 7,022,856 | B2 | 4/2006 | Sawuer et al. | 514/292 |
| 7,034,027 | B2 | 4/2006 | Shultze et al. | 544/343 |
| 7,034,047 | B2 | 4/2006 | Junji et al. | 514/383 |
| 2002/0006443 | A1 | 1/2002 | Babcock et al. | |
| 2002/0150616 | A1 | 10/2002 | Vandecruys et al. | |
| 2002/0173502 | A1 | 11/2002 | Allerton et al. | |
| 2003/0153575 | A1 | 8/2003 | Bomburn et al. | |
| 2004/0067945 | A1 | 4/2004 | Niewohner et al. | |

FOREIGN PATENT DOCUMENTS

| | | |
|---|---|---|
| EP | 0526004 | 7/1992 |
| EP | 0595546 | 3/1996 |
| EP | 0799823 | 2/1997 |
| EP | 0995750 | 10/1999 |
| EP | 0995751 | 10/1999 |
| EP | 1092718 | 10/2000 |
| EP | 1092719 | 10/2000 |
| EP | 1241170 | 9/2002 |
| EP | 1293503 | 3/2003 |
| JP | 00063363 | 8/1998 |
| WO | WO 93/06104 | 4/1993 |
| WO | WO 93/07149 | 4/1993 |
| WO | WO 95/19978 | 7/1995 |
| WO | WO 97/13755 | 4/1997 |
| WO | WO 98/47890 | 10/1998 |
| WO | WO 00/15228 | 3/2000 |
| WO | WO 00/23433 | 4/2000 |
| WO | WO 00/35298 | 6/2000 |
| WO | WO 01/58880 * | 8/2001 |

OTHER PUBLICATIONS

Coco, A.S., *American Family Physician*, "Primary dysmenorrhoea", vol. 60, pp. 489-496 (1999).

Finnin, et al., *Journal Pharm Science*, 'Transdermal Penetration Enhancers': Applications, Limitations, and potential, vol. 88 (10), 955-958, (1999).

Kakefuda, et al., *Bioorganic & Medicinal Chemistry*, "Discovery of 4,5-Diphenyl-1,2,4-trizole Derivatives as a Novel Class of Selective antagonists for the Human $V_{1A}$ Receptor", vol. 10, p. 1905-1912, (2002).

Kakefuda, et al., *Journal of Medicinal Chemistry*, "Synthesis and Pharmacological evaluation of 5-4(4-Biphenyl)-3-methyl-4-phenyl-1,2,4-trizole Derivatives as a Novel Class of Selective antagonists for the Human $V_{1A}$ Receptor", vol. 45, p. 2589-2598, (2002).

Liang, et al. *Expert Opinion in Therapeutic Patents*, "Fast-dissolving intraoral drug deliver system", vol. 11 (6), 981-986, (2001).

Rotella, et al., *Journal of Medicinal Chemistry*, "N-3-Substituted Imidazoquinazolinones: Potent and Selective PDE5 Inhibitors as Potential Agents for Treatment of Erectile Dysfunction." vol. 43(7), 1257-1263, (2000).

Schroeder, et al, *Pediatric Clinics of North America*, "J.S. Dysmenorrhoea and pelvic pain in adolescents", vol. 46, pp. 555-571 (1999).

Verma et al., *Pharmaceutical Technology On-line*, "Drug delivery technologies and future directions", vol. 25(2), 1-14,(2001).

* cited by examiner

TRIAZOLE DERIVATIVES WHICH INHIBIT VASOPRESSIN ANTAGONISTIC ACTIVITY

This application is a 371 of PCT/IB05/00079 filed Jan. 11, 2005 which claims benefit of U.S. Provisional Application 60/549,407 filed Mar. 1, 2004.

This invention relates to novel compounds useful in therapy and to processes for the preparation of such compounds. It also relates to compositions containing such compounds, their use and intermediates used in their preparation.

WO 01/87855 discloses triazole derivatives as inhibitors of glycine transporter activity. WO 01/58880 and JP2000-63363 disclose triazole derivatives useful as arginine Vassopressin $V_{1A}$ receptor antagonists. Kakefuda et al., Bioorg. Med. Chem. 10 (2002) 1905-1912 and Kakefuda et al., J.Med-.Chem., 2002, 45, 2589-2598 discuss the utility of 4,5-diphenyl-1,2,4-triazole derivatives as selective antagonists for the human $V_{1A}$ receptor and comment that the 4,5-diphenyl-1,2,4-triazole structure plays an essential role in $V_{1A}$ affinity.

The compounds of the present invention have been found to have useful pharmaceutical properties. They may be used to treat aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis.

Particularly of interest are the following diseases or disorders:
anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor and Raynaud's disease.

In particular, the compounds of the present invention exhibit vasopressin antagonist activity and can be used in the treatment of dysmenorrhoea (primary and secondary).

There is a high unmet need in the area of menstrual disorders and it is estimated that up to 90% of all menstruating women are affected to some degree. Up to 42% of women miss work or other activities due to menstrual pain and it has been estimated that around 600 million work hours a year are lost in the US as a result {Coco, A. S. (1999), Primary dysmenorrhoea, [Review] [30 refs], *American Family Physician*, 60, 489-96,}.

Menstrual pain in the lower abdomen is caused by myometrial hyperactivity and reduced uterine blood flow. These pathophysiological changes result in abdominal pain that radiates out to the back and legs. This may result in women feeling nauseous, having headaches and suffering from insomnia. This condition is called dysmenorrhoea and can be classified as either primary or secondary dysmenorrhoea.

Primary dysmenorrhoea is diagnosed when no abnormality causing the condition is identified. This affects up to 50% of the female population {Coco, A. S. (1999), Primary dysmenorrhoea, [Review] [30 refs], *American Family Physician*, 60, 489-96; Schroeder, B. & Sanfilippo, J. S. (1999). Dysmenorrhoea and pelvic pain in adolescents, [Review] [78 refs] *Pediatric Clinics of North America*, 46, 555-71}. Where an underlying gynaecological disorder is present, such as endometriosis, pelvic inflammatory disease (PID), fibroids, or cancers, secondary dysmenorrhoea will be diagnosed. Secondary dysmenorrhoea is diagnosed in only approximately 25% of women suffering from dysmenorrhoea. Dysmenorrhoea can occur in conjunction with menorrhagia, which accounts for around 12% of referrals to gynaecology outpatients departments.

Currently, women suffer from primary dysmenorrhoea are treated with non-steroidal anti-inflammatory drugs (NSAID's) or the oral contraceptive pill. In cases of secondary dysmenorrhoea surgery may be undertaken to correct the underlying gynaecological disorder.

Women suffering from dysmenorrhoea have circulating vasopressin levels which are greater than those observed in healthy women at the same time of the menstrual cycle. Inhibition of the pharmacological actions of vasopressin, at the uterine vasopressin receptor, may prevent dysmenorrhoea.

According to the present invention there is provided a compound of formula (I),

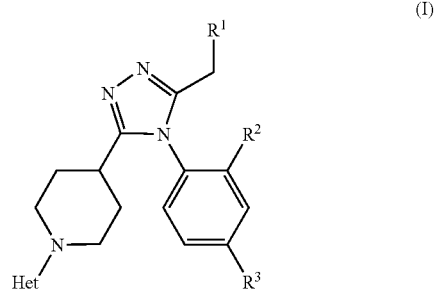

(I)

or a pharmaceutically acceptable derivative thereof, wherein:
Het represents 2-pyridinyl or 2-pyrimidinyl;
$R^1$ represents H, $C_{1-3}$ alkyl or a nitrogen-containing heterocyclic ring;
$R^2$ represents H, benzyl or $C_{1-3}$ alkyl; and
$R^3$ represents H, methyl, methoxy or chloro.

In the above definitions, alkyl groups containing three carbon atoms, except where indicated, can be unbranched or branched chain. Examples of alkyl include methyl, ethyl, n-propyl and i-propyl.

Unless otherwise stated, the term heterocyclic ring, heterocyclic or heterocycle, means a five- or six-membered saturated, unsaturated or aromatic ring containing one or more heteroatoms selected from N, S and O. Preferred heterocycles included within the above definition are triazolyl, piperidinyl and morpholinyl.

Preferred aspects of the invention are as set out below:
a compound according to formula (I) wherein Het represents 2-pyridinyl;
a compound according to formula (I) or aspect 1 wherein $R^1$ represents 1,2,3-triazolyl;
a compound according to formula (I) or either of aspects (i) or (ii) wherein $R^2$ represents H or methyl;

a compound according to formula (I) or any of aspects (i) to (iii) wherein $R^3$ represents chloro;

a compound according to formula (I) or aspect (iii) wherein at least one of $R^1$, $R^2$ and $R^3$ represents a group other than H;

a compound according to formula (I) wherein $R^1$ represents 1,2,3-triazolyl and/or $R^3$ represents chloro.

Preferred compounds according to the present invention are:

2-{4-[4-(2-Ethyl-phenyl)-5-methyl-4H-[1,2,4]triazol-3-yl]-piperidin-1-yl}-pyrimidine;

2-{4-[5-Methyl-4-(2-propyl-phenyl)-4H-[1,2,4]triazol-3-yl]-piperidin-1-yl}-pyrimidine 2-{4-[4-(2-Isopropyl-phenyl)-5-methyl-4H-[1,2,4]triazol-3-yl]-piperidin-1-yl}-pyrimidine 4-(5-Morpholin-4-ylmethyl-4-phenyl-4H-[1,2,4]triazol-3-yl)-3,4,5,6-tetrahydro-2H-[1,2']bipyridinyl;

4-(5-Butyl-4-phenyl-4H-[1,2,4]trizaol-3-yl)-3,4,5,6-tetrahydro-2H-[1,2']bipyridinyl;

4-(4-Phenyl-5-piperidin-1-ylmethyl-4H-[1,2,4]triazol-3-yl)-3,4,5,6-tetrahydro-2H-[1,2']bipyridinyl;

4-(5-Methyl-4-phenyl-4H-[1,2,4]triazol-3-yl)-3,4,5,6-tetrahydro-2H-[1,2']bipyridinyl;

4-[4-(4-Methoxy-2-methyl-phenyl)-5-methyl-4H-[1,2,4]triazol-3-yl]-3,4,5,6-tetrahydro-2H-[1,2']bipyridinyl;

4-[4-(4-Chloro-2-methyl-phenyl)-5-methyl-4H-[1,2,4]triazol-3-yl]-3,4,5,6-tetrahydro-2H-[1,2']bipyridinyl;

4-(5-Methyl-4-o-tolyl-4H-[1,2,4]triazol-3-yl)-3,4,5,6-tetrahydro-2H-[1,2']bipyridinyl;

4-[4-(4-Chloro-phenyl)-5-methyl-4H-[1,2,4]triazol-3-yl]-3,4,5,6-tetrahydro-2H-[1,2']bipyridinyl;

4-[4-(4-Methoxy-phenyl)-5-[1,2,3]triazol-2-ylmethyl-4H-[1,2,4]triazol-3-yl]-3,4,5,6-tetrahydro-2H-[1,2']bipyridinyl;

4-[4-(4-Methoxy-phenyl)-5-methyl-4H-[1,2,4]triazol-3-yl]-3,4,5,6-tetrahydro-2H-[1,2']bipyridinyl;

4-(4-o-Tolyl-5-[1,2,3]triazol-2-ylmethyl-4H-[1,2,4]triazol-3-yl)-3,4,5,6-tetrahydro-2H-[1,2']bipyridinyl;

4-[4-(4-Chloro-2-methyl-phenyl)-5-[1,2,3]triazol-2-ylmethyl-4H-[1,2,4]triazol-3-yl]-3,4,5,6-tetrahydro-2H-[1,2']bipyridinyl;

4-(4-Phenyl-5-[1,2,3]triazol-2-ylmethyl-4H-[1,2,4]triazol-3-yl)-3,4,5,6-tetrahydro-2H-[1,2']bipyridinyl;

4-[4-(4-Chloro-phenyl)-5-[1,2,3]triazol-2-ylmethyl-4H-[1,2,4]triazol-3-yl]-3,4,5,6-tetrahydro-2H-[1,2']bipyridinyl;

4-(5-Methyl-4-p-tolyl-4H-[1,2,4]triazol-3-yl)-3,4,5,6-tetrahydro-2H-[1,2']bipyridinyl;

4-[4-(2,4-Dimethyl-phenyl)-5-methyl-4H-[1,2,4]triazol-3-yl]-3,4,5,6-tetrahydro-2H-[1,2']bipyridinyl;

4-[4-(4-Chloro-2-methyl-phenyl)-5-morpholin-4-ylmethyl-4H-[1,2,4]triazol-3-yl]-3,4,5,6-tetrahydro-2H-[1,2']bipyridinyl; and pharmaceutically acceptable derivatives thereof.

Pharmaceutically acceptable derivatives of the compounds of formula (I) according to the invention include salts, solvates, complexes, polymorphs, prodrugs, stereoisomers, geometric isomers, tautomeric forms, and isotropic variations of compounds of formula (I). Preferably, pharmaceutically acceptable derivatives of compounds of formula (I) comprise salts, solvates, esters and amides of the compounds of formula (I). More preferably, pharmaceutically acceptable derivatives of compounds of formula (I) are salts and solvates.

The pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, D- and L-lactate, malate, maleate, malonate, mesylate, methylsulphate, naphthylate, 2-napsylate, nicotinate, nitrate, orotate, oxalate, palmitate, palmoate, phosphate, hydrogen phosphate, dihydrogen phosphate, saccharate, stearate, succinate, sulphate, D- and L-tartrate, tosylate and trifluoroacetate salts. A particularly suitable salt is the besylate derivative of the compounds of the present invention.

Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts see Stahl and Wermuth, Handbook of Pharmaceutical Salts: Properties, Selection and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components what may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) and pharmaceutically acceptable derivatives include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labelled compounds of formula (I).

As stated, the invention includes all polymorphs of the compounds of formula (I) as hereinbefore defined.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, hydrolytic cleavage. Such derivatives are referred to as "prodrugs". Further information on the use of prodrugs may be found in "Pro-drugs as Novel Delivery Systems, Vol. 14, ACS Symposium Series (T Higuchi and W Stella) and "Bioreversible Carriers in Drug Design", Pergamon Press, 1987 (ed. E B Roche, American Pharmaceutical Association).

Prodrugs in accordance with the invention can, for example, be produced by replacing appropriate functionalities present in the compounds of formula (I) with certain moieties know to those skilled in the art as "pro-moieties" as described, for example, in "Design of Prodrugs" by H Bundgaard (Elsevier, 1985).

Some examples of prodrugs in accordance with the invention include:

where the compound of formula (I) contains a carboxylic acid functionality (—COOH), an ester thereof, for example, replacement of the hydrogen with $(C_1-C_8)$alkyl;

where the compound of formula (I) contains an alcohol functionality (—OH), an ether thereof, for example, replacement of the hydrogen with $(C_1-C_6)$alkanoyloxymethyl; and where the compound of formula (I) contains a primary or secondary amino functionality (—NH$_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Also within the scope of the invention are the metabolites of the compounds of formula (I) when formed in vivo following administration of a compound of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible, and where the compound contains, for example, a keto or oxime group or an aromatic moiety, tautomeric isomerism ('tautomerism') may occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral HPLC.

Alternatively, the racemate (or racemic precursor) may be reacted with a suitable optically active compound, for example, an alcohol, or, in the case where the compounds of formula (I) contains an acidic or basic moiety, an acid or base such as tartaric acid or 1-phenylethylamine. The resulting diastereomeric mixture may be separated by chromatography and/or fractional crystallisation and one or both of the diastereomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention also includes all pharmaceutically acceptable isotopic variations of a compound of the formula (I) one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as $^2$H and $^3$H, carbons such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulphur such as $^{35}$S, fluorine such as $^{18}$F, iodine such as $^{123}$I and $^{125}$I, and chlorine such as $^{36}$Cl.

Certain isotopically-labelled compounds of formula (I), for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Pharmaceutically acceptable solvates in accordance with the invention include those wherein the solvent of crystallisation may be isotopically substituted, e.g. D$_2$O, d$_6$-acetone and d$_6$-DMSO.

Unless otherwise provided herein:

Et$_3$N means triethylamine;

AcOH means acetic acid;

MeOH means methanol, EtOH means ethanol, and EtOAc means ethyl acetate;

THF means tetrahydrofuran, DCM means dichloromethane, DMF means N,N-dimethylformamide and NMP means N-methyl-2-pyrrolidinone;

Boc means tert-butoxy carbonyl, CBz means benzyloxy carbonyl;

Me means methyl, Et means ethyl, Bu means butyl, Cl means chloro; OH means hydroxy; and LG means a suitable leaving group;

p-TSA means p-toluenesulphonic acid;

Pd$_2$(Dba)$_3$ means bis(dibenzylideneacetone)palladium;

NMM means N-Methylmorpholine;

WSCDI means 1-(3-dimethylaminopropyl)-3-ethylcarbodiimide hydrochloride;

DCC means N,N'-dicyclohexylcarbodiimide;

HOAT means 1-hydroxy-7-azabenzotriazole;

HOBT means 1-hydroxybenzotriazole hydrate;

PyBOP® means Benzotriazol-1-yloxytris(pyrrolidino) phosphoniumhexafluoro phosphate;

PyBrOP® means bromo-tris-pyrrolidino-phosphonium-hexafluoro phosphate;

Mukaiyama's reagent means 2-chloro-1-methylpyridinium iodide;

Hünig's base means N-ethyldiisopropylamine;

Prot means protecting group;

TFA means trifluoroacetic acid;

halo means halogen; and triflic anhydride means Trifluoromethanesulfonic acid anhydride.

The following Schemes 1.0 to 6.2 illustrate the preparation of compounds of the formula (I), throughout which HET and $R^1$ to $R^3$ are as hereinbefore defined:

Scheme 1.0

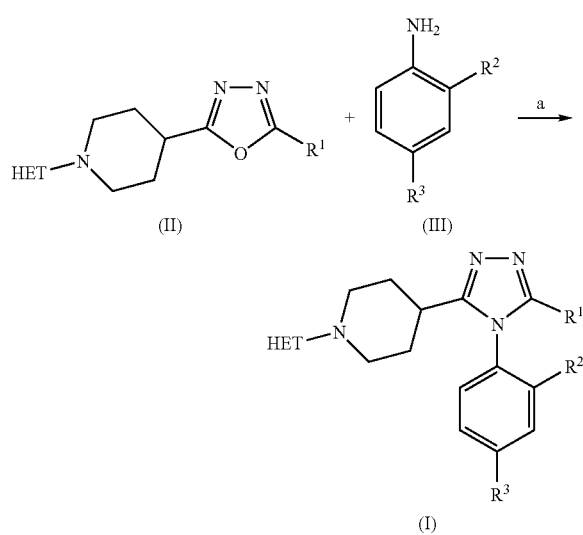

Amines suitable for use as compound (III) are commercially available or are known in the literature.

Scheme 2.

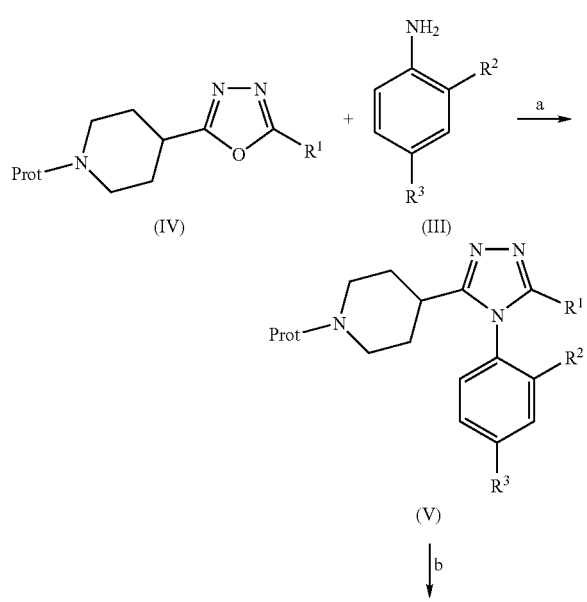

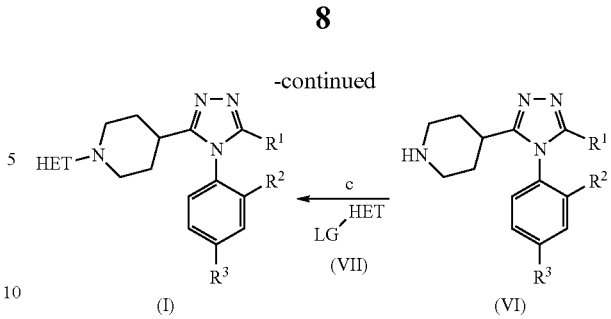

Prot represents a suitable protecting group for nitrogen. Standard methodology for nitrogen protecting groups is used, such as that found in textbooks, (e.g. "Protecting Groups in Organic Synthesis" by T. W. Greene and P. Wutz).

LG represents a leaving group such as halogen, preferably Br.

Compounds suitable for use as compound (VII) are commercially available or are known in the literature.

Step (a): Amine (III) is reacted with oxadiazole (II & IV) to give a compound of formula (I). This reaction is carried out by heating the starting materials to elevated temperatures such as 100-200° C. for 15 minutes to 18 hours and optionally at elevated pressures, or optionally under microwave radiation, with a suitable acidic catalyst such as p-TSA or trifluoroacetic acid, or Lewis acid catalyst such as magnesium chloride, optionally using a high boiling solvent such as xylene or toluene.

Preferred conditions are: 1.5 eq. of amine (III) with 0.1 eq. magnesium chloride at 150° C. for 4 to 18 hours, optionally at elevated pressures; or 3 to 4 eq. amine (III) with 0.25 eq. pTSA in xylene at 150° C. for 18 hours; or 2 eq. amine (III), 1 eq. TFA in xylene or toluene, at between 110 to 150° C.

Step (b): Deprotection of compound (V) is undertaken using standard methodology, as described in "Protecting Groups in Organic Synthesis" by T. W. Greene and P. Wutz".

When Prot is Boc the preferred method is hydrogen chloride in a suitable solvent such as 1,4-dioxane at room temperature for 1 to 16 hours, or a solution of trifluoroacetic acid in dichloromethane for 1 to 2 hours.

When Prot is CBz the preferred methods is hydrogenolysis using a suitable palladium catalyst in a solvent such as ethanol.

When Prot is an allyl carbamate, preferred conditions are thiobenzoic acid and a suitable palladium catalyst such as $Pd_2(Dba)_3$ with a suitable phosphine additive such as 1,4-bis(diphenylphosphino)butane in tetrahydrofuran for 20 minutes.

Step (c): Arylation of compound (VI) can be carried out by a palladium catalysed cross-coupling reaction with compound (VII) using a suitable base (t-BuONa), a catalytic amount of suitable additive such as 2,2'-bis(diphenylphosphino)-1,1'-binaphthyl and a suitable palladium catalyst. The reaction is carried out in toluene at an elevated temperature for 1 to 24 hours, under an inert atmosphere, to give compound (I). Alternatively compound (I) can be prepared by reacting amine (VI) with compound (VII) at an elevated temperature, such as 50° C. to 140° C., in a suitable solvent, such as DMF, NMP or 1,4-dioxan, for about 1 to 48 hours in the presence of a base such as potassium carbonate, sodium hydrogen carbonate or Hünig's base.

Preferred conditions are: 1.3 eq. halide (VII), 1 to 2 eq. potassium carbonate in N,N-dimethylformamide at 60° C. for 4 to 18 hours.

Compounds suitable for use as compounds (II) and (IV) are known in the literature or can be prepared as shown in Schemes 3.1 and 3.2.

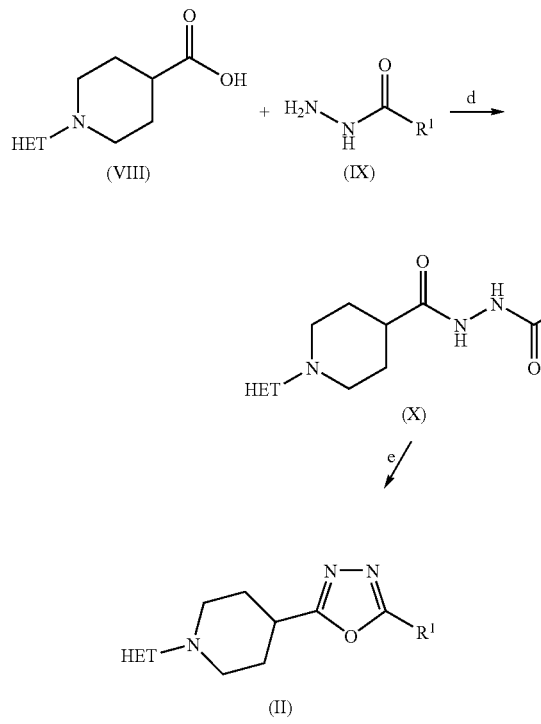

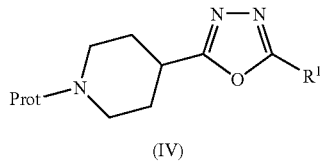

(IV)

Compounds (VIII)/(VIII') and (IX) are either commercially available or are known in methodology such as the hydrolysis of the corresponding ester. (see Preparation 2)

Step (d): The reaction of carboxylic acid (VIII/VIII') with hydrazide (IX) can be carried out by standard methods.

Coupling may be undertaken by using either:

(i) an acyl chloride derivative of acid (VIII/VIII')+hydrazide (IX), with an excess of acid acceptor in a suitable solvent; or (ii) the acid (VIII/VIII') with a conventional coupling agent+hydrazide (IX), optionally in the presence of a catalyst, with an excess of acid acceptor in a suitable solvent.

Typically the conditions are as follows:

acid chloride of acid (VIII/VIII') (generated in-situ), an excess of hydrazide, optionally with an excess of 3° amine such as $Et_3N$, Hünig's base or NMM, in DCM or THF, without heating for 1 to 24 hrs; or (ii) acid (VIII/VIII'), WSCDI/DCC and HOBT/HOAT, an excess of hydrazide, with an excess of NMM, $Et_3N$, Hünig's base in THF, DCM or EtOAc, at room temperature for 4 to 48 hours; or acid (VIII/VIII'), PYBOP®/PyBrOP®/Mukaiyama's reagent, an excess of hydrazide, with an excess of NMM, $Et_3N$, Hünig's base in THF, DCM or EtOAc, at room temperature for 4 to 24 hours.

The preferred conditions are: acid chloride of acid (VIII/VIII') (generated in-situ), 1.2 to 2 eq. Hydrazide (IX) in DCM at room temperature for 18 hours, in the presence of 1 to 1.2 eq. of N-methylmorpholine; or the carboxylic acid (VIII/VIII'), 1 eq. HOBT, 1 eq. WSCDI, 1.2 eq. hydrazide (IX) in dichloromethane at room temperature for 18 hours.

Step (e): Cyclisation of compound (X/X') is carried out under suitable dehydrating conditions, at elevated temperatures for up to 18 hours.

Typically, dehydrating agents such as polyphosphonic acid, phosphorous oxychloride, of triflic anhydride with pyridine, optionally in a suitable solvent such as dichloromethane, are used at temperatures from 50 to 120° C. for 5 minutes to 12 hours. Optionally the reaction can be carried out under an inert atmosphere. Alternatively, the oxadiazole (II & IV) may be prepared according to the method of Rigo et. al. Synth. Commun. 16(13), 1665, 1986.

Preferred conditions are: Phosphorous oxychloride at 100 to 110° C. for 1 to 2 hours.

Alternative routes to compound (X/X') are shown below in Schemes 4.1 and 4.2:

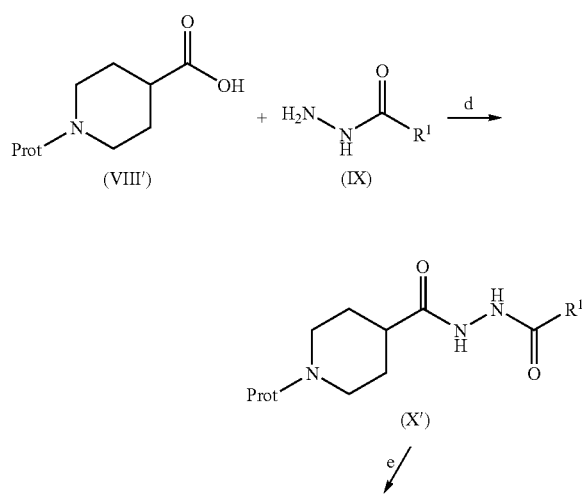

Scheme 4.1

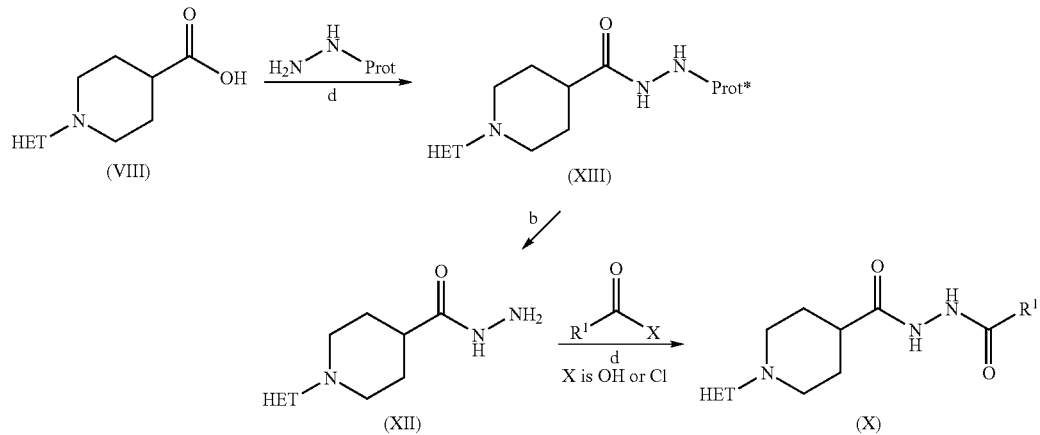

Scheme 4.2

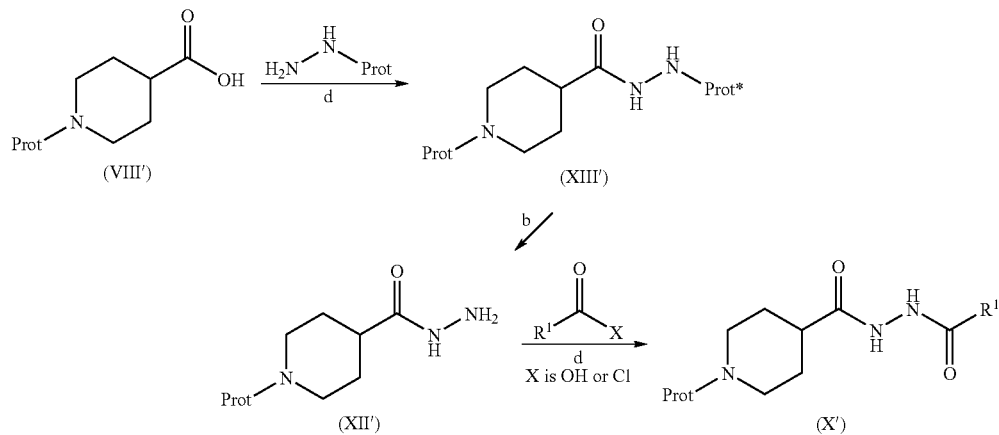

Carboxylic acid (VIII/VIII') and a protected hydrazine, where Prot* is typically Boc, may be coupled to give compound (XIII/XIII'), using the conditions described for the preparation of (X/X') above. Prot* is then removed using standard methodology as described in step (b), to give (XII/XII').

Compound (X/X') may then be obtained by the coupling of hydrazide (XII/XII') with a carboxylic acid, or it's derivative [R¹C(O)X, where X is OH or Cl], under the conditions described previously for step (d).

Alternative routes to compound (XII/XII') are shown below in Schemes 5.1 and 5.2:

-continued

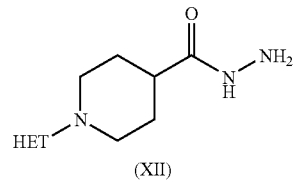

Scheme 5.1

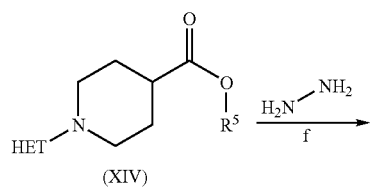

Scheme 5.2

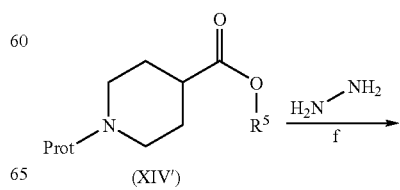

-continued

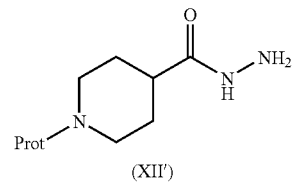

(XII')

Step (f): The ester (XIV/XIV') may be reacted with hydrazine in a suitable solvent, such as methanol at elevated temperature to provide the hydrazide (XII/XII').

Preferred conditions: 3 eq. hydrazine, in methanol, at reflux for 18 hours.

When $R^1$ represents a nitrogen containing heterocyclic ring (represented in the following schemes as

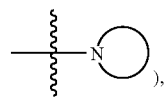

), compounds of the formula (I/V') may be prepared according to the routes described in Schemes 6.1 and 6.2:

Scheme 6.1

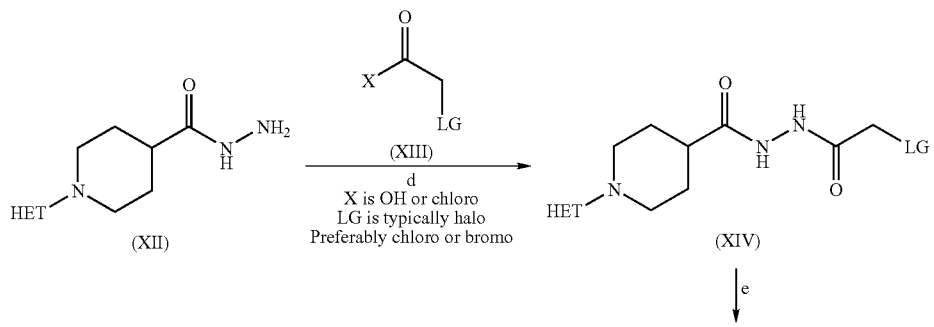

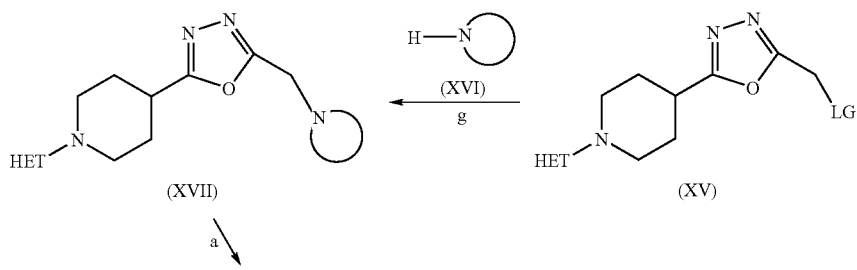

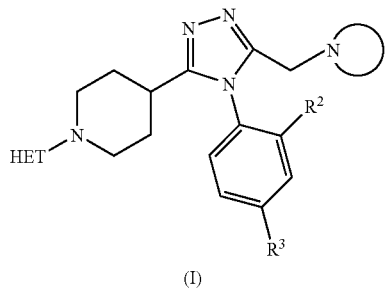

(I)

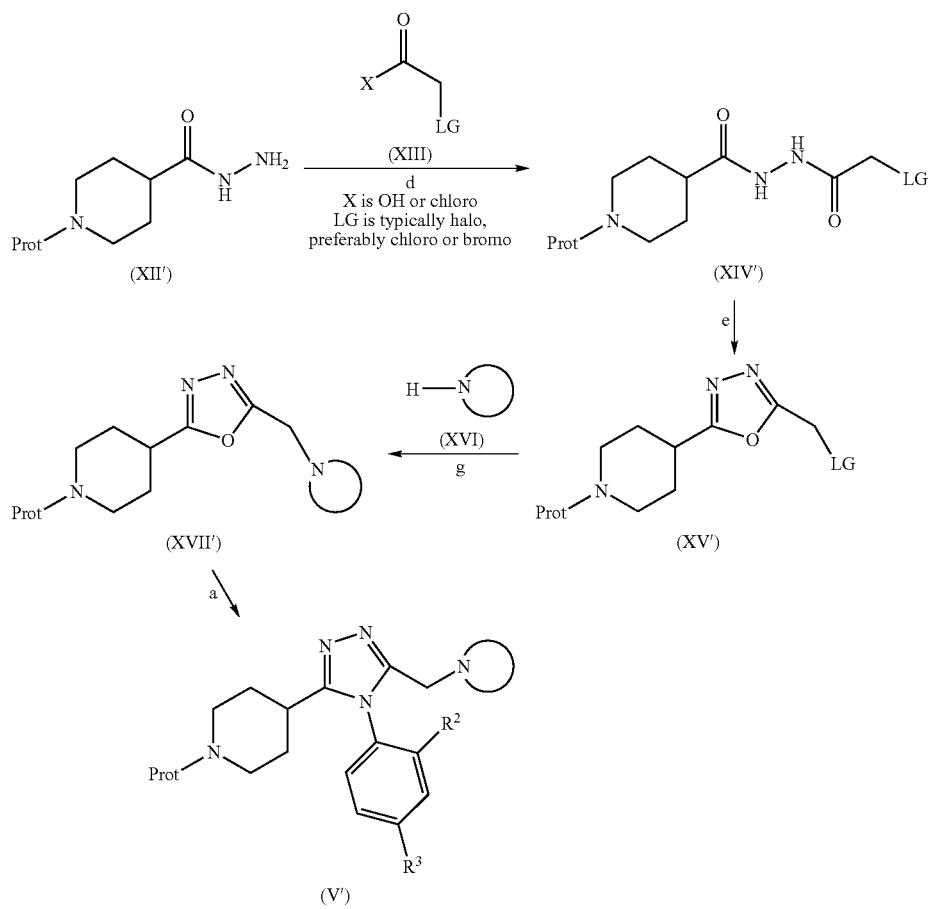

Scheme 6.2

Compounds suitable for use as compound (XIII) and (XVI) are commercially available or are known in the literature.

Step (d): Coupling of compound (XIII) with hydrazide (XII/XII') may be carried out using standard methodology as outlined above.

Step (e): Dehydration and cyclisation of compound (XIV/XIV') to give oxadiazole (XV/XV') is achieved by the methodology outlined above.

Step (g): Compound (XV/XV') is reacted with amine (XVI) to give compound (XVII/IV') in the presence of an excess of base, such as triethylamine, Hünig's base or potassium carbonate as proton acceptor. The reaction is conducted in a suitable high boiling solvent, such as toluene or DMF, at temperatures from 50° C. to 100° C. for 1 to 24 hours.

Alternatively a palladium catalysed cross-coupling reaction can be carried out using a suitable base (t-BuONa), a catalytic amount of a suitable additive, such as tri n-butyl phosphine, and a suitable palladium catalyst in toluene at reflux from 12 to 24 hours under an inert atmosphere.

Preferred conditions are: 1 eq. of amine, 2 eq. of potassium carbonate in DMF at 60° C. for 3 to 4 hours.

Step (a): Amination of compound (XVII/IV') to give compound (I/V') is carried out using the methodology outlined above.

It will be appreciated by those skilled in the art that, when appropriate, the order of steps (a) and (g) may be reversed.

Compound (V') may then be converted to compounds of formula (I), according to the reactions described in Scheme 2.

It will be apparent to those skilled in the art that sensitive functional groups may need to be protected and deprotected during synthesis of a compound of formula (I/V'). This may be achieved by conventional techniques, for example as described in "Protective Groups in Organ Synthesis" by T W Greene and P G M Wuts, John Wiley and Sons Inc. 1991.

The compounds of the present invention are useful because they possess pharmacological activity in animals. In particular they are useful in the treatment of a number of conditions including aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis sleep disorder, spinal cord injury, thrombosis, urogenital tract infection, urolithiasis. Particularly of interest is dysmenorrhoea (primary or secondary), more particularly, primary dysmenorrhoea.

Thus, according to another aspect of the invention, there is provided a method of treatment of dysmenorrhoea which comprises administering a therapeutically effective amount of a compound of the invention to a patient suffering from anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease. The use of the compounds as a medicament and the use of the compounds of the present invention in the manufacture of a medicament for the treatment of anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease, particular dysmenorrhoea, are also provided.

Compounds of the invention intended for pharmaceutical use may be administered as crystalline or amorphous products. They may be obtained, for example, as solid plugs, powders, or films by methods such as precipitation, crystallisation, freeze drying, spray drying, or evaporative drying. Microwave or radio frequency drying may be used for this purpose.

They may be administered alone or in combination with one or more other compounds of the invention or in combination with one or more other drugs (or as any combination thereof). The compounds of the present invention may be administered in combination with an oral contraceptive. Thus in a further aspect of the invention, there is provided a pharmaceutical product containing an V1a antagonist and an oral contraceptive as a combined preparation for simultaneous, separate or sequential use in the treatment of dysmenorrhoea.

The compounds of the present invention may be administered in combination with a PDE5 inhibitor. Thus in a further aspect of the invention, there is provided a pharmaceutical product containing a V1a antagonist according to the present invention and a PDEV inhibitor as a combined preparation for simultaneous, separate or sequential use in the treatment of dysmenorrhoea.

PDEV inhibitors useful for combining with V1a antagonists include, but are not limited to:

The PDE5 inhibitors mentioned in International Patent Application publication nos. WO03/000691; WO02/64590; WO02/28865; WO02/28859; WO02/38563; WO02/36593; WO02/28858; WO02/00657; WO02/00656; WO02/10166; WO02/00658; WO01/94347; WO01/94345; WO00/15639 and WO00/15228;

The PDE5 inhibitors mentioned in U.S. Pat. Nos. 6,143, 746, 6,143,747 and 6,043,252;

the pyrazolo [4,3-d]pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in published international patent application WO 93/07149; the quinazolin-4-ones disclosed in published international patent application WO 93/12095; the pyrido [3,2-d] pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo [4,3-d]pyrimidin-7-ones disclosed in published international patent application WO 99/54333; the pyrazolo [4,3-d]pyrimidin-4-ones disclosed in EP-A-0995751; the pyrazolo [4,3-d] pyrimidin-7-ones disclosed in published international patent application WO 00/24745; the pyrazolo [4,3-d]pyrimidin-4-ones disclosed in EP-A-0995750; the hexahydropyrazino [2'; 1',6,1]pyrido [3,4-b]indole-1,4-diones disclosed in published international application WO95/19978; the pyrazolo [4,3-d] pyrimidin-4-ones disclosed in WO00/27848; the imidazo[5, 1-f][1,2,4]triazin-ones disclosed in EP-A-1092719 and in published international application WO 99/24433 and the bicyclic compounds disclosed in published international application WO 93/07124; the pyrazolo [4,3-d]pyrimidin-7-ones disclosed in published international application WO 01/27112; the pyrazolo [4,3-d]pyrimidin-7-ones disclosed in published international application WO 01/27113; the compounds disclosed in EP-A-1092718 and the compounds disclosed in EP-A-1092719; the tricyclic compounds disclosed in EP-A-1241170; the alkyl sulphone compounds disclosed in published international application WO 02/074774; the compounds disclosed in published international application WO 02/072586, the compounds disclosed in published international application WO 02/079203 and the compounds disclosed in WO 02/074312.

Preferably 5-[2-ethoxy-5-(4-methyl-1-piperazinylsulphonyl)phenyl]-1-methyl-3-n-propyl-1,6-dihydro-7H-pyrazolo [4,3-d]pyrimidin-7-one (sildenafil, e.g. as sold as Viagra®) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H--pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/ 54333); 5-[2-ethoxy-5-(4-ethylpiperazin-1-ylsulphonyl) pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo [4,3-d]pyrimidin-7-one (see WO01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R,12aR)-2,3,6,7,12,12a-hexahydro-2-methyl-6-(3,4-methylenedioxyphenyl)pyrazino[2',1':6,1]pyrido[3,4-b]indole-1,4-dione (tadalafil, IC-351, Cialis®), i.e. the compound of examples 78 and 95 of published international application WO95/19978, as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil, LEVITRA®) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 of published international application WO93/07124 (EISAI); compounds 3 and 14 from Rotella D P, *J. Med. Chem.*, 2000, 43, 1257; 4-(4-chlorobenzyl)amino-6,7,8-trimethoxyquinazoline; N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide["DA-8159" (Example 68 of WO00/27848)]; and 7,8-dihydro-8-oxo-6-[2-propoxyphenyl]-1H-imidazo[4,5-g]quinazoline and 1-[3-[1-[(4-fluorophenyl)methyl]-7,8-dihydro-8-oxo-1H-imidazo[4,5-g]quinazolin-6-yl]-4-propoxyphenyl]carboxamide.

4-bromo-5-(pyridylmethylamino)-6-[3-(4-chlorophenyl)-propoxy]-3(2H)pyridazinone, 1-[4-[(1,3-benzodioxol-5-yl-methyl)amino]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer); FR229934 and FR226807 (Fujisawa); and Sch-51866.

The contents of the published patent applications and journal articles and in particular the general formulae of the therapeutically active compounds of the claims and exemplified compounds therein are incorporated herein in their entirety by reference thereto.

Preferably the PDEV inhibitor is selected from sildenafil, tadalafil, vardenafil, DA-8159 and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one.

Most preferably the PDE5 inhibitor is sildenafil and pharmaceutically acceptable salts thereof. Sildenafil is a preferred salt.

The compounds of the present invention may be administered in combination with an NO donor. Thus in a further aspect of the invention, there is provided a pharmaceutical product containing a V1a antagonist according to the present invention and a NO donor as a combined preparation for simultaneous, separate or sequential use in the treatment of dysmenorrhoea.

The compounds of the present invention may be administered in combination with L-arginine, or as an arginate salt. Thus in a further aspect of the invention, there is provided a pharmaceutical product containing a V1a antagonist according to the present invention and L-arginine as a combined preparation for simultaneous, separate or sequential use in the treatment of dysmenorrhoea.

The compounds of the present invention may be administered in combination with a COX inhibitor. Thus in a further aspect of the invention, there is provided a pharmaceutical product containing a V1a antagonist according to the present invention and a COX inhibitor as a combined preparation for simultaneous, separate or sequential use in the treatment of dysmenorrhoea.

COX inhibitors useful for combining with the compounds of the present invention include, but are not limited to:

ibuprofen, naproxen, benoxaprofen, flurbiprofen, fenoprofen, fenbufen, ketoprofen, indoprofen, piprofen, carprofen, oxaprozin, prapoprofen, miroprofen, tioxaprofen, suprofen alminoprofen, tiaprofenic acid, fluprofen, bucloxic acid, indomethacin, sulindac, tolmetin, zomepirac, diclofenac, fenclofenec, alcofenac, ibufenac, isoxepac, furofenac, tiopinac, zidometacin, acetyl salicylic acid, indometacin, piroxicam, tenoxicam, nabumetone, ketorolac, azapropazone, mefenamic acid, tolfenamic acid, diflunisal, podophyllotoxin derivatives, acemetacin, droxicam, floctafenine, oxyphenbutazone, phenylbutazone, proglumetacin, acemetacin, fentiazac, clidanac, oxipinac, mefenamic acid, meclofenamic acid, flufenamic acid, niflumic acid, flufenisal, sudoxicam, etodolac, piprofen, salicylic acid, choline magnesium trisalicylate, salicylate, benorylate, fentiazac, clopinac, feprazone, isoxicam and 2-fluoro-a-methyl[1,1'-biphenyl]-4-acetic acid, 4-(nitrooxy)butyl ester (See Wenk, et al., *Europ. J. Pharmacol.* 453:319-321 (2002));

meloxicam, (CAS registry number 71125-38-7; described in U.S. Pat. No. 4,233,299), or a pharmaceutically acceptable salt or prodrug thereof;

Substituted benzopyran derivatives that are described in U.S. Pat. No. 6,271,253. Also benzopyran derivatives described in U.S. Pat. Nos. 6,034,256 and 6,077,850 along with International Publication No's WO 98/47890 and WO 00/23433;

Chromene COX2 selective inhibitors described in U.S. Pat. Nos. 6,077,850 and 6,034,256;

The compounds described in International Patent Application Publication No's WO 95/30656, WO 95/30652, WO 96/38418 and WO 96/38442, and the compounds described in European Patent Application Publication No. 799823, along with the pharmaceutically acceptable derivatives thereof;

celecoxib (U.S. Pat. No. 5,466,823), valdecoxib (U.S. Pat. No. 5,633,272), deracoxib (U.S. Pat. No. 5,521,207), rofecoxib (U.S. Pat. No. 5,474,995), etoricoxib (International Patent Application Publication No. WO 98/03484), JTE-522 (Japanese Patent Application Publication No. 9052882), or a pharmaceutically acceptable salt or prodrug thereof;

Parecoxib (described in U.S. Pat. No. 5,932,598), which is a therapeutically effective prodrug of the tricyclic Cox-2 selective inhibitor valdecoxib (described in U.S. Pat. No. 5,633,272), in particular sodium parecoxib;

ABT-963 (described in International Patent Application Publication No. WO 00/24719)

Nimesulide (described in U.S. Pat. No. 3,840,597), flosulide (discussed in J. Carter, *Exp. Opin. Ther. Patents*, 8(1), 21-29 (1997)), NS-398 (disclosed in U.S. Pat. No. 4,885,367), SD 8381 (described in U.S. Pat. No. 6,034,256), BMS-347070 (described in U.S. Pat. No. 6,180,651), S-2474 (described in European Patent Publication No. 595546) and MK-966 (described in U.S. Pat. No. 5,968,974);

The compounds and pharmaceutically acceptable derivatives described in U.S. Pat. Nos. 6,395,724, 6,077,868, 5,994, 381, 6,362,209, 6,080,876, 6,133,292, 6,369,275, 6,127,545, 6,130,334, 6,204,387, 6,071,936, 6,001,843, 6,040,450, International Patent Application Publication No WO 96/03392, International Patent Application Publication No WO 96/24585, U.S. Pat. Nos. 6,340,694, 6,376,519, 6,153,787, 6,046,217, 6,329,421, 6,239,137, 6,136,831, 6,297,282, 6,239,173, 6,303,628, 6,310,079, 6,300,363, 6,077,869, 6,140,515, 5,994,379, 6,028,202, 6,040,320, 6,083,969, 6,306,890, 6,307,047, 6,004,948, 6,169,188, 6,020,343, 5,981,576, 6,222,048, 6,057,319, 6,046,236, 6,002,014, 5,945,539, 6,359,182, International Patent Application Publication No. WO 97/13755, International Patent Application Publication No. WO 96/25928, International Patent Application Publication No. WO 96/374679, International Patent Application Publication No. WO 95/15316, International Patent Application Publication No. WO 95/15315, International Patent Application Publication No. WO 96/03385, International Patent Application No. WO 95/00501, International Patent Application No. WO 94/15932, International Patent Application Publication No. WO 95/00501, International Patent Application Publication No. WO 94/27980, International Patent Application Publication No. WO 96/25405, International Patent Application Publication No. WO 96/03388, International Patent Application Publication No. WO 96/03387, U.S. Pat. No. 5,344,991, International Patent Application Publication No. WO 95/00501, International Patent Application Publication No. WO 96/16934, International Patent Application Publication No. WO 96/03392, International Patent Application Publication No. WO 96/09304, International Patent Application Publication No. WO 98/47890, and International Patent Application Publication No. WO 00/24719.

The contents of any of the patent applications, and in particular the general formulae of the therapeutically active compounds of the claims and exemplified compound therein, are incorporated herein in their entirety by reference thereto.

Generally, the compounds of the present invention will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19$^{th}$ Edition (Mack Publishing Company, 1995).

Thus, according to another aspect of the present invention, there is provided a pharmaceutical formulation comprising a compound of formula (I) in admixture with a pharmaceutically acceptable adjuvant, diluent or carrier.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example water, ethanol, polyethylene glycol, propylene glycol, methylcellulose, or a suitable oil, and one or more emulsifying agents and/or suspending agents. Liquid formulations may also be prepared by the reconstitution of a solid, for example from a sachet.

The compounds of the invention may also be used in fast-dissolving, fast disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt %, of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % and 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt %, of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted- and programmed release.

Suitable modified release formulations for the purpose of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intreperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled-, targeted- and programmed release. Thus, compounds of the invention may be formulated as a solid, semisolid, or thixotropic liquid for administration as an implanted depot providing modified release of the active compound. Examples of such formulations include drug-coated stents and PGLA microspheres.

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci. 88 (10), 955-958 by Finnin and Morgan (October 1999).

Other means of topical administration include delivery of iontrophoresis, electroporation, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer or nebuliser contains a solution or suspension of the compound(s) of the invention comprising, for example, ethanol, aqueous ethanol, or a suitable alternative agent for dispersing, solubilising or extending release of the active, the propellant(s) as solvent and an optional surfactant, such as sorbitan trioleate, oleic acid or an oligolactic acid.

Prior to use in a dry powder of suspension formulation, the drug product is micronised to a size suitable for delivery by inhalation (typically less than 5 microns). This may be achieved by any appropriate comminuting method, such a spiral jet milling, fluid be jet milling, supercritical fluid processing to form nanoparticles, high pressure homogenisation or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typically formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly-DL-lactic-coglycolic acid (PGLA). Modified release formulations include delayed-, sustained-, pulsed-, controlled-, targeted and programmed release.

The compounds of the invention may be administered rectally or vaginally, for example, in the form of a suppository, pessary or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontrophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities such as cyclodextrin or polyethylene glycol-containing polymers to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compounds of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention will typically be in the range of from about 0.01 to about 15 mg/kg of body weight, depending on the mode of administration. The total daily dose may be administered in a single dose or divided doses throughout the day. These dosages are based on an average human subject having a weight of about 65 kg to 70 kg. The physician will readily be able to determine doses for subjects whose weight falls outside this range, such as infants and the elderly.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (either on a temporary or permanent basis) of, or prevention of symptoms and disorders associated with primary and/or secondary dysmenorrhoea. The treatment may be a pre-treatment as well as a treatment at the on-set of symptoms.

The compounds of the present invention may be tested in the screens set out below.

1.0 $V_{1A}$ Filter Binding Assay 1.1 Membrane Preparation

Receptor binding assays were performed on cellular membranes prepared from CHO cells stably expressing the human $V_{1A}$ receptor, (CHO-h$V_{1A}$). The CHO-h$V_{1A}$ cell line was kindly provided under a licensing agreement by Marc Thibonnier, Dept. of Medicine, Case Western Reserve University School of Medicine, Cleveland, Ohio. CHO-h$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. For bulk production of cell pellets, adherent CHO-h$V_{1A}$ cells were grown to confluency of 90-100% in 850 $cm^2$ roller bottles containing a medium of DMEM/Hams F12 Nutrient Mix supplemented with 10% fetal bovine serum, 2 mM L-glutamine and 15 mM HEPES. Confluent CHO-h$V_{1A}$ cells were washed with phosphate-buffered saline (PBS), harvested into ice cold PBS and centrifuged at 1,000 rpm. Cell pellets were stored at −80° C. until use. Cell pellets were thawed on ice and homogenised in membrane preparation buffer consisting of 50 mM Tris-HCl, pH 7.4, 5 mM $MgCl_2$ and supplemented with a protease inhibitor cocktail, (Roche). The cell homogenate was centrifuged at 1000 rpm, 10 min. 4° C. and the supernatant was removed and stored on ice. The remaining pellet was homogenised and centrifuged as before. The supernatants were pooled and centrifuged at 25,000×g for 30 min at 4° C. The pellet was resuspended in freezing buffer consisting of 50 mM Tris-HCl, pH 7.4, 5 mM $MgCl_2$ and 20% glycerol and stored in small aliquots at −80° C. until use. Protein concentration was determined using Bradford reagent and BSA as a standard.

1.2 $V_{1A}$ Filter Binding

Protein linearity followed by saturation binding studies were performed on each new batch of membrane. Membrane concentration was chosen that gave specific binding on the linear portion of the curve. Saturation binding studies were then performed using various concentrations of [$^3$H]-arginine vasopressin, [$^3$H]-AVP (0.05 nM-100 nM) and the $K_d$ and $B_{max}$ determined.

Compounds were tested for their effects on [$^3$H]-AVP binding to CHO-h$V_{1A}$ membranes, ($^3$H-AVP; specific activity 65.5 Ci/mmol; NEN Life Sciences). Compounds were solubilised in dimethylsulfoxide (DMSO) and diluted to working concentration of 10% DMSO with assay buffer containing 50 mM Tris-HCL pH 7.4, 5 mM $MgCl_2$ and 0.05% BSA, 25 µl compound and 25 µl [$^3$H]-AVP, (final concentration at or below $K_d$ determined for membrane batch, typically 0.5 nM-0.6 nM) were added to a 96-well round bottom polypropylene plate. The binding reaction was initiated by the addition of 200 µl membrane and the plates were gently shaken for 60 min at room temperature. The reaction was terminated by rapid filtration using a Filtermate Cell Harvester (Packard Instruments) through a 96-well GF/B UniFilter Plate which had been presoaked in 0.5% polyethyleneimine to prevent peptide sticking. The filters were washed three times with 1 ml ice cold wash buffer containing 50 mM Tris-HCL pH 7.4 and 5 mM $MgCl_2$. The plates were dried and 50 µl Microscint-0 (Packard Instruments) was added to each well. The plates were sealed and counted on a TopCount Microplate Scintillation Counter (Packard Instruments). Non-specific binding (NSB) was determined using 1 μM unlabelled d(CH2)5Tyr(Me)AVP ([β-mercapto-β,β-cyclopentamethylenepropionyl,0-Me-Tyr$^2$,Arg$^8$]-vasopressin) (βMCPVP), (Sigma). The radioligand binding data was analysed using a four parameter logistic equation with the min forced to 0%. The slope was free fitted and fell between −0.75 and −1.25 for valid curves. Specific binding was calculated by subtracting the mean NSB cpm from the mean Total cpm. For test compounds the amount of ligand bound to the receptor was expressed as % bound=(sample cpm−means NSB cpm)/specific binding cpm×100. The % bound was plotted against the concentration of test compound and a sigmoidal curve was fitted. The inhibitory dissociation constant ($K_i$) was calculated using the Cheng-Prusoff equation: $K_i=IC_{50}/(1+[L]/K_d)$ where [L] is the concentration of ligand present in the well and $K_d$ is the dissociation constant of the radioligand obtained from Scatchard plot analysis.

2.0 $V_{1A}$ Functional Assay; Inhibition of AVP/$V_{1A}$-R Mediated Ca$^{2+}$ Mobilization by FLIPR (Fluorescent Imaging Plate Reader) (Molecular Devices)

Intracellular calcium release was measured in CHO-h$V_{1A}$ cells using FLIPR, which allows the rapid detection of calcium following receptor activation. The CHO-h$V_{1A}$ cell line was kindly provided under a licensing agreement by Marc Thibonnier, Dept. of Medicine, Case Western Reserve University School of Medicine, Cleveland, Ohio. CHO-$V_{1A}$ cells were routinely maintained at 37° C. in humidified atmosphere with 5% CO$_2$ in DMEM/Hams F12 nutrient mix supplemented with 10% fetal bovine serum, 2 mM L-glutamine, 15 mM HEPES and 400 μg/ml G418. On the afternoon before the assay cells were plated at a density of 20,000 cells per well into black sterile 96-well plates with clear bottoms to allow cell inspection and fluorescence measurements from the bottom of each well. Wash buffer containing Dulbecco's phosphate buffered saline (DPBS) and 2.5 mM probenecid and loading dye consisting of cell culture medium containing 4 μM Fluo-3-AM (dissolved in DMSO and pluronic acid) (Molecular Probes) and 2.5 mM probenecid was prepared fresh on the day of assay. Compounds were solubilised in DMSO and diluted in assay buffer consisting of DPBS containing 1% DMSO, 0.1% BSA and 2.5 mM probenecid. The cells were incubated with 100 μl loading dye per well for 1 hour at 37° C. in humidified atmosphere with 5% CO$_2$. After dye loading the cells were washed three times in 100 μl wash buffer using a Denley plate washer. 100 μl wash buffer was left in each well. Intracellular fluorescence was measured using FLIPR. Fluorescence readings were obtained at 2 s intervals with 50 μl of the test compound added after 30 s. An additional 155 measurements at 2 s intervals were then taken to detect any compound agonistic activity. 50 μl of arginine vasopressin (AVP) was then added so that the final assay volume was 200 μl. Further fluorescence readings were collected at 1 s intervals for 120 s. Responses were measured as peak fluorescence intensity (FI). For pharmacological characterization a basal FI was subtracted from each fluorescence response. For AVP dose response curves, each response was expressed as a % of the response to the highest concentration of AVP in that row. For IC$_{50}$ determinations each response was expressed as a % of the response to AVP. IC50 values were converted to a modified $K_b$ value using the Cheng-Prusoff equation which takes into account the agonist concentration, [A], the agonist EC$_{50}$ and the slope: $K_b=IC_{50}/(2+[A]/A_{50}]^n)^{1/n}−1$ where [A] is the concentration of AVP, $A_{50}$ is the EC$_{50}$ of AVP from the dose response curve and n=slope of the AVP dose response curve.

The compounds of the invention may have the advantage that they are more potent, have a longer duration of action, have a broader range of activity, are more stable, have fewer side effects or are most selective, or have other more useful properties than the compounds of the prior art.

The invention is illustrated by the following preparations and examples:

Preparation 1: 2-[4-(5-Methyl-[1,3,4]oxadiazol-2-yl)-piperidin-1-yl]-pyrimidine

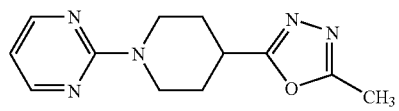

4-(5-Methyl-[1,3,4]oxadiazole-2-yl)-piperidine hydrochloride (203 mg, 1 mmol) (see reference WO 0039125, preparation 43) was added to a solution of 2-bromopyrimidine (207 mg, 1.3 mmol) and potassium carbonate (207 mg, 1.5 mmol) in N,N-dimethylformamide (0.5 mL). The solution was heated to 60° C. for 4 hours, before cooling and stirring at room temperature for 18 hours. The solvent was evaporated under reduced pressure, and the residue partitioned between water and dichloromethane. The aqueous layer was extracted with dichloromethane, and the combined organic layers were washed with brine, before being dried over magnesium sulphate and evaporated under reduced pressure. The residue was purified by chromatography on silica gel (25 g) eluting with dichloromethane and methanol (97.5:2.5) to give the title compound as a crystalline solid (75 mg).

$^1$H NMR (400 MHz, CDCl$_3$): δ 1.76-1.92 (m, 2H), 2.02-2.17 (m, 2H), 2.45 (s, 3H), 3.05-3.19 (m, 3H), 4.63-4.76 (m, 2H), 6.44 (t, 1H), 8.26 (d, 2H); LRMS: m/z ES$^+$ 246 [M+H]$^+$

Preparation 2: 3,4,5,6-Tetrahydro-2H-[1,2']bipyridinyl-4-carboxylic acid

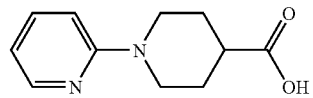

Sodium hydroxide solution (5M, 24.8 ml, 0.12 mol) was added drop wise to a solution of 3,4,5,6-tetrahydro-2H-[1,2'] bipyridinyl-4-carboxylic acid ethyl ester (5.8 g, 24 mmol) (see reference Farmaco, 1993, 48(10), 1439) in 1,4-dioxane (100 mL). The mixture was stirred at room temperature for 72 hours and then evaporated under reduced pressure. The residue was purified by ion exchange chromatography on Dowex® 50 WX8 resin using methanol:0.88 ammonia:water as eluant (gradient from 0:0:100 to 0:5:95 to 5:5:90). The material obtained was triturated with diethyl ether to give the title compound (4.42 g); LCMS: m/z ES+ 288 [M+H]+

Preparation 3: 3,4,5,6-Tetrahydro-2H-[1,2']bipyridi-nyl-4-carboxylic acid N'-(2-morpholin-4-yl-acetyl)-hydrazide

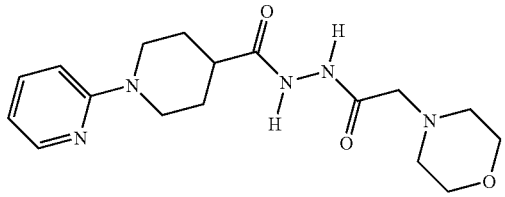

The acid of Preparation 2 (0.5 g, 2.4 mmol) was suspended in dichloromethane (20 mL) containing N,N-dimethylforma-mide (2 drops) and oxalyl chloride (1.27 mL, 14 mmol) in dichloromethane (5 mL) was added dropwise. The mixture was stirred for 2 hours at room temperature and then was evaporated under reduced pressure. The yellow solid was suspended in dichloromethane (5 mL) and N-methylmorpho-line (0.32 mL, 2.9 mmol) added cautiously. Morpholin-4-yl-acetic acid hydrazide (462 mg, 2.9 mmol) (see reference Bull. Soc. Chim. Fr. 1962, 250) was added, and the mixture was then stirred at room temperature for 18 hours. The reaction was diluted into dichloromethane (100 mL) and washed with aqueous sodium hydrogen carbonate. The aqueous layer was extracted with dichloromethane and the combined organic layers were dried over magnesium sulphate, filtered and evaporated under reduced pressure. The residue was tritu-rated with ethyl acetate, to give the title compound as a solid (306 mg)
¹H NMR (400 MHz, CDCl₃): δ 1.94 (m, 4H), 2.60 (s, 5H), 2.79 (s, 2H), 2.99 (m, 2H), 3.72 (m, 4H), 4.33 (d, 2H), 6.63 (m, 1H), 6.73 (d, 1H), 7.51 (m, 1H), 8.14 (m, 1h), 8.82 (s, 1H), 9.22 (broad s, 1H); LRMS m/z ES+ 348 [M+H]+

Preparation 4: 4-(5-Morpholin-4-ylmethyl-[1,3,4]oxadiazol-2-yl)-3,4,5,6-tetrahydro-2H -[1,2']bipy-ridinyl

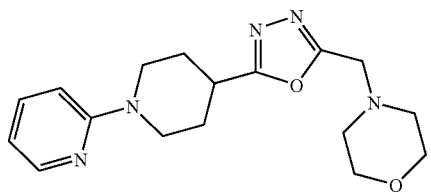

Phosphorus oxychloride (1.0 mL, 10.73 mmol) was added to the hydrazide of Preparation 3 (200 mg, 0.58 mmol and the suspension was heated to 110° C. for 90 minutes. After cool-ing, acetonitrile was added to give a brown solution to which water was added, and then basified using aqueous sodium carbonate. The mixture was then extracted with ethyl acetate (2×100 mL), and the combined extracts dried over magne-sium sulphate and evaporated under reduced pressure. The residue was crystallised from ethyl acetate and pentane to give the title compound as a sandy coloured solid.

¹H NMR (400 MHz, CD₃OD): δ 1.91 (m, 2H), 2.16 (m, 2H), 2.57 (m, 4H), 3.11 (m, 2H), 3.30 (m, 1H), 3.70 (m, 4H), 3.80 (s, 2H), 2.24 (m, 2H), 6.64 (m, 1H), 6.86 (m, 1H), 7.56 (m, 1H), 8.05 (m, 1H); LRMS m/z ES+ 330 [M+H]+

Preparation 5: 3,4,5,6-Tetrahydro-2H-[1,2']bipyridi-nyl-4-carboxylic acid N'-acetyl-hydrazide

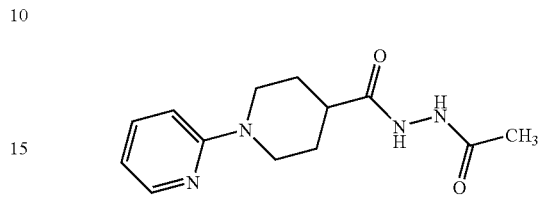

Oxalyl chloride (17 mL, 0.18 mol) was added drop wise to a suspension of the acid from Preparation 2 (8.0 g, 38.79 mmol) in dichloromethane (150 mL) at 0° C. The mixture was stirred at room temperature for 2.5 hours. Oxalyl chloride and dichloromethane were evaporated under reduced pressure. The residue was dissolved in dichloromethane (200 mL) and acetic hydrazide (3.45 g, 45.57 mmol) was added in small portions, followed by N-methylmorpholine (4.26 mL, 38.75 mmol). The mixture was then stirred at room temperature for 18 hours. The mixture was evaporated under reduced pres-sure, and the residue partitioned between ethyl acetate and aqueous hydrochloric acid (3M). The aqueous layer was washed with ethyl acetate, then basified to pH10 with sodium hydroxide pellets before extracting with ethyl acetate. The combined organic layers were evaporated under reduced pressure, and the resulting white solid was triturated with diethyl ether to give the title compound (4.6 g).
¹H NMR (400 MHz, CD₃OD): δ 1.70-1.82 (m, 2H), 1.90 (m, 2H), 1.98 (s, 3H), 2.53 (m, 1H), 2.90 (t, 2H), 4.29 (d, 2H), 6.63 (m, 1H), 6.83 (d, 1H), 7.53 (m, 1H), 8.05 (m, 1H); LRMS: m/z APCl+ 263 [M+H]+

Preparation 6: 4-(5-Methyl-[1,3,4]oxadiazol-2-yl)-3,4,5,6-tetrahydro-2H-[1,2']bipyridinyl

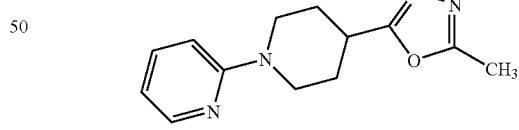

The title compound was obtained as a yellow solid (1.38 g, 82% yield) from the hydrazide of Preparation 5 (1.81 g, 6.9 mmol) and phosphorus oxychloride (12 mL, 128 mmol) fol-lowing the procedure described in Preparation 4. The residue obtained was purified by flash chromatography using a 20 g Isolute® cartridge, eluting with a solvent gradient of dichlo-romethane:methanol (100:0 to 95:5 by volume).
¹H NMR (400 MHz, CD₃OD): δ 1.88 (m, 2H), 2.15 (m, 2H), 2.52 (s, 3H), 3.09 (t, 2H), 3.23 (m, 1H), 4.27 (d, 2H), 6.66 (m, 1H), 6.86 (d, 1H), 7.55 (m, 1H), 8.08 (m, 1H); LRMS: m/z APCl+ 245 [M+H]+

Preparation 7: 3,4,5,6-Tetrahydro-2H-[1,2']bipyridinyl-4-carboxylic acid N'-pentanoyl-hydrazide

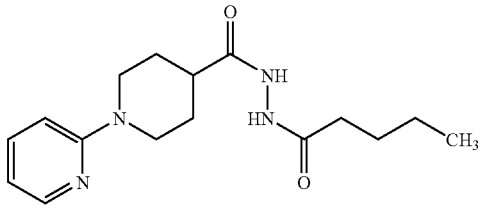

The carboxylic acid from Preparation 2 (1.5 g, 7.3 mmol) was suspended in dichloromethane (40 mL) containing N,N-dimethylformamide (2 drops) and oxalyl chloride (1.27 mL, 14 mmol) in dichloromethane (5 mL) was added dropwise. The mixture was stirred for 5 hours at room temperature and then evaporated under reduced pressure. The residue was suspended in hexane and evaporate (3×20 mL). The residue was dissolved in dichloromethane and cooled to 0° C. and pentanoic acid hydrazide (1.7 g, 14.6 mmol) was added. 1-Methyl-pyrrolidin-2one (1.6 mL, 14.6 mmol) in dichloromethane (10 mL) was added drop wise and the mixture was stirred at room temperature for 16 hours. The solvent was evaporated under reduced pressure and the residue was triturated with diethyl ether. The material obtained was dissolved in water and acidified to pH 2 by addition of 2N hydrochloric acid. The acidic solution was filtered and the filtrate was washed with ethyl acetate (3×20 mL) then basified with sodium carbonate. The solid formed was triturated with diethyl ether and isolated by filtration to give the title compound as a white solid (0.68 g).

LCMS: m/z ES⁻ 303 [M−H]⁻

Preparation 8: 4-(5-Butyl-[1,3,4]oxadiazol-2-yl)-3,4,5,6-tetrahydro-2H-[1,2']bipyridinyl

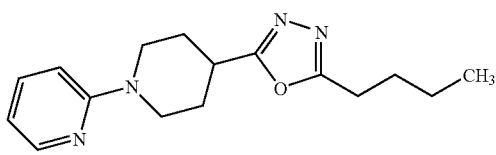

The hydrazide from Preparation 7 (2.5 g, 8.71 mmol) was combined with phosphorus oxychloride (25 mL) and heated to 100° C. for 2 hours, after which time the mixture was poured onto iced water with care. The mixture was then extracted into ethyl acetate, and then dried over magnesium sulphate. The residue was evaporated under reduced pressure to give a beige solid which was triturated with ethyl acetate, and then purified by chromatography on silica gel, eluting with a gradient of ethyl acetate:pentane (20:80 to 25:75). The title compound was obtained as an off-white solid (500 mg).

LRMS: m/z ES⁺ 287 [M+H]⁺

Preparation 9: 3,4,5,6-Tetrahydro-2H-[1,2']bipyridinyl-4-carboxylic acid hydrazide

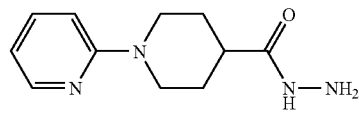

3,4,5,6-Tetrahydro-2H-[1,2']bipyridinyl-4-carboxylic acid ethyl ester (35 g, 150 mmol) (see reference Farmaco, 1993, 48(10), 1439) was dissolved in methanol (700 mL) containing hydrazine hydrate (34 mL, 150 mmol) and was heated under reflux for 18 hours. After this time, more hydrazine hydrate (22.7 mL, 100 mmol) was added and the mixture stirred for a further 18 hours. The mixture was cooled to room temperature and evaporated under reduced pressure. The solid formed was triturated with ethyl acetate to give the title compound as a white solid.

¹H NMR (400 MHz, CD₃OD): δ 1.99 (m, 4H), 2.20 (m, 1H), 2.85 (t, 2H), 4.50 (d,2H), 6.30 (m, 1H), 7.30 (d, 1H), 7.70 (t, 1H), 8.40 (d, 1H).

Preparation 10: 3,4,5,6-Tetrahydro-2H-[1,2']bipyridinyl-4-carboxylic acid N'-(2-chloro-acetyl)-hydrazide

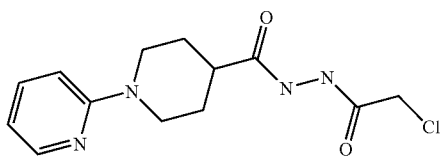

The hydrazide of Preparation 9 (23.6 g, 0.11 mol) was suspended in dichloromethane (500 mL) and 4-methylmorpholine (17.7 mL, 0.16 mol) was added. The mixture was cooled using an ice bath and chloroacetyl chloride (12.8 mL, 0.16 mol) was added dropwise. The reaction was warmed to room temperature and was stirred for 3 hours. The solid formed was isolated by filtration, washed with dichloromethane and diethyl ether, and dried under vacuum to give the title compound (20.4 g).

LCMS: m/z ES⁺ 297 [M+H]⁺

Preparation 11: 4-(5-Chloromethyl-[1,3,4]oxadiazol-2-yl)-3,4,5,6-tetrahydro-2H-[1,2']bipyridinyl

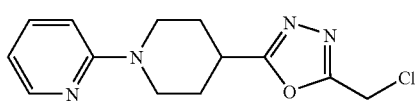

The hydrazide of Preparation 10 (20.4 g, 69 mmol) was suspended in phosphorus oxychloride (150 mL) at 100° C. for 4 hours. The mixture was cooled and the solvent was evaporated under reduced pressure. The residue was dissolved in ethyl acetate and was added to water. The aqueous layer was basified by addition of solid sodium hydrogen carbonate and the phases were separated. The aqueous phase was extracted with ethyl acetate (×2) and the combined organic layers were dried over magnesium sulphate and evaporated under reduced pressure. The material isolated was triturated with diethyl ether to give the title compound as a beige solid (15 g).

¹H NMR (400 MHz, CD₃OD): δ 1.91 (m, 2H), 2.19 (m, 2H), 3.14 (m, 2H), 3.30 (m, 1H), 4.29 (m, 2H), 4.86 (s, 2H), 6.69 (m, 1H), 6.89 (d, 1H), 7.58 (m, 1H), 8.08 (d, 1H)

Preparation 12: 4-(5-Piperidin-1-ylmethyl-[1,3,4] oxadiazol-2-yl)-3,4,5,6-tetrahydro-2H -[1,2']bipyridinyl

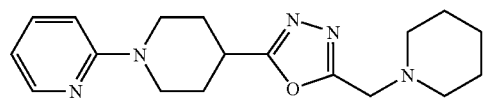

The chloromethyl compound of Preparation 11 (0.5 g, 1.8 mmol) was added to piperidine (0.18 mL, 1.8 mmol) and potassium carbonate (0.5 g, 3.6 mmol) in N,N-dimethylformamide (8 mL) and the mixture was heated at 60° C. for 3 hours. The reaction mixture was evaporated under reduced pressure and the residue was partitioned between water and ethyl acetate. The organic solution was washed with water and then with 2N hydrochloric acid and the combined aqueous solutions were basified with solid sodium hydrogen carbonate. The aqueous mixture was extracted with ethyl acetate (×3) and the combined organic layers were dried over magnesium sulphate and evaporated under reduced pressure. The residue was purified by chromatography on silica gel using methanol:0.88 ammonia:dichloromethane as eluant (2:0.25:98) to give the title compound as a pale pink solid (0.48 g).

LCMS: m/z ES⁺ 328 [M+H]⁺

Preparation 13: 4-(5-[1,2,3]Triazol-2-ylmethyl-[1,3,4]oxadiazol-2-yl)-3,4,5,6-tetrahydro-2H-[1,2']bipyridinyl

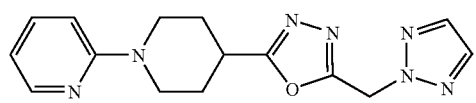

The chloromethyl compound of Preparation 11 (5 g, 17.9 mmol) was combined with potassium carbonate (4.97 g, 36.0 mmol), 1,2,3-triazole (1.04 mL, 17.9 mmol) and N,N-dimethylformamide (70 mL), and then heated to 60° C. with stirring for 4 hours. The solvent was evaporated under reduced pressure and the residue was partitioned between dichloromethane and water. The aqueous layer was washed with dichloromethane and the combined organic layers were dried over magnesium sulphate and then evaporated under reduced pressure to give an orange oil. This oil was purified by flash chromatography on silica gel eluting with a solvent gradient of dichloromethane:methanol:0.88 ammonia (98:2:0.25 to 97:3:0.25 by volume). The title compound was obtained after trituration from diethyl ether as a white solid (2.0 g).

¹H NMR (400 MHz, CD₃OD): δ 1.82 (m, 2H), 2.11 (m, 2H), 3.07 (t, 2H), 3.23 (m, 1H), 4.22 (d, 2H), 4.80 (s, 2H), 6.64 (d, 1H), 6.84 (d, 1H), 7.54 (t, 1H), 7.76 (s, 2H), 8.07 (d, 1H).

LRMS: m/z APCl⁺312 [M+H]⁺

EXAMPLE 1

2-{4-[4-(2-Ethyl-phenyl)-5-methyl-4H-[1,2,4]triazol-3-yl]-piperidin-1-yl}-pyrimidine

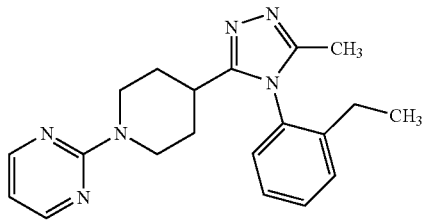

The oxadiazole of Preparation 1 (100 mg, 0.41 mmol) was combined with 2-ethylphenylamine (0.075 mL, 0.61 mmol), and magnesium (II) chloride (10 mg, 0.10 mmol) in a sealed vessel and heated to 150° C. for 18 hours. Ther reaction mixture was dissolved in dichloromethane and washed with citric acid (10% aqueous), and sodium hydrogen carbonate (saturated aqueous solution). The organic layer was evaporated under reduced pressure, and the residue was purified on silica gel using Isco Systems Combiflash® Sg100c on an Isco Systems Redisep 10 g cartridge, eluting with dichloromethane and methanol (gradient from 100:0 to 95:5). This afforded the title compound (43.6 mg).

¹H NMR (400 MHz, CDCl₃): δ 1.15 (t, 3H), 1.76-1.89 (m, 3H), 2.00-2.12 (m, 1H), 2.16 (s, 3H), 2.28 (q, 2H), 2.56 (m, 1H), 2.85 (q, 2H), 4.71 (dd, 2H), 6.42 (t, 1H), 7.09 (d, 1H), 7.37 (t, 1H), 7.49 (m, 2H), 8.24 (d, 2H); LRMS: m/z ES⁺ 349 [M+H]⁺

EXAMPLES 2 TO 7

The compounds of the following tabulated examples of the general formula:

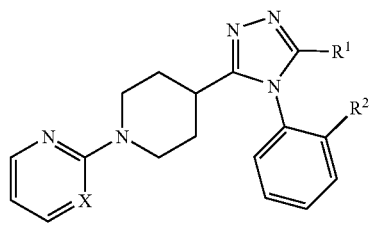

were prepared by a similar method to that of Example 1 using the appropriate oxadiazole starting material, and the corresponding anilines.

| Eg. | R¹ | R² | X | Analytical Data |
|---|---|---|---|---|
| 2 | CH₃ | 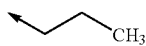 | N | ¹H NMR (400MHz, CDCl₃): δ 0.89 (t, 3H), 1.54 (m, 2H), 1.75-1.87 (m, 4H), 2.17 (s, 3H), 2.23 (t, 2H), 2.55 (m, 1H), 2.79-2.90 (m, 2H), 4.65-4.79 (dd, 2H), 6.42 (t, 1H), 7.09 (d, 1H), 7.37 (t, 1H), 7.47 (m, 2H), 8.25 (d, 2H). LRMS m/z ES⁺ 363 [M + H]⁺ |
| 3[1] | CH₃ | 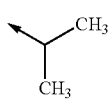 | N | ¹H NMR (400MHz, CDCl₃): δ 1.17 (dd, 6H). 1.72-1.88 (m, 4H), 2.18 (s, 3H), 2.43 (m, 1H), 2.52 (m, 1H), 2.77-2.90 (m, 2H), 4.67 (d, 1H), 4.80 (d, 1H), 6.43 (t, 1H), 7.06 (d, 1H), 7.36 (t, 1H), 7.53 (m, 2H), 8.26 (d, 2H). LRMS m/z ES⁺ 363 [M + H]⁺ |
| 4[2] | 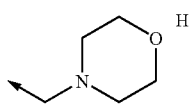 | H | C | ¹H NMR (400MHz, CD₃OD): δ 1.84 (m, 4H), 2.31 (m, 4H), 2.74 (m, 2H), 2.83 (m, 1H), 3.50 (s, 6H), 4.24 (d, 2H), 6.62 (m, 1H), 6.81 (d, 1H), 7.49 (m, 3H), 7.61 (m, 3H), 8.02 (m, 1H). LRMS m/z ES⁺ 405 [M + H]⁺ |
| 5[3] | 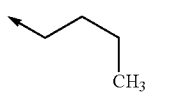 | H | C | ¹H NMR (400MHz, CD₃OD): δ 0.84 (t, 3H), 1.28 (m, 2H), 1.54 (m, 2H), 1.89 (m, 4H), 2.59 (t, 2H), 2.79 (m, 3H), 4.27 (m, 2H), 6.63 (t, 1H), 6.80 (d, 1H), 7.45 (m, 2H), 7.51 (t, 1H), 7.64 (m, 3H), 8.02 (d, 1H). LRMS m/z ES⁺ 384 [M + Na]⁺ |
| 6[4] | 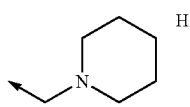 | H | C | ¹HNMR (400MHz, CD₃OD): δ 1.33-1.44 (m, 6H), 1.90 (m, 4H), 2.27 (m, 4H), 2.76 (m, 2H), 2.86 (m, 1H), 3.44 (s, 2H), 4.27 (m, 2H), 6.62 (t, 1H), 6.81 (d, 1H), 7.47-7.54 (m, 3H), 7.61 (m, 3H), 8.02 (d, 1H). LRMS m/z ES⁺ 403 [M + H]⁺ |
| 7[5] | CH₃ | | H | C | ¹HNMR (400MHz, CD₃OD): δ 1.85 (m, 4H), 2.25 (s, 3H), 2.70-2.85 (m, 3H), 4.25 (d, 2H), 6.62 (m, 1H), 6.80 (d, 1H), 7.44-7.55 (m, 3H), 7.62-7.69 (m, 3H), 8.03 (d, 1H). LRMS m/z ES⁺ 320 [M + H]⁺ |

[1] Non sealed vessel

[2] 3 equivalents of aniline. Non-sealed vessel, 4 hours heating. Product was triturated from ethyl acetate.

[3] 3 equivalents of aniline (1.26 mmol), 15 mg of MgCl₂ used. Non-sealed vessel. After chromatography product was triturated from diethyl ether.

[4] equivalents of aniline used (1.24 mmol). Non-sealed vessel. After chromatography product was crystallised from ethyl acetate:pentane.

[5] 2 equivalents of aniline used (2.26 mmol)

EXAMPLE 8

4-[4-(4-Methoxy-2-methyl-phenyl)-5-methyl-4H-[1,2,4]triazol-3-yl]-3,4,5,6-tetrahydro-2H-[1,2']bipyridinyl

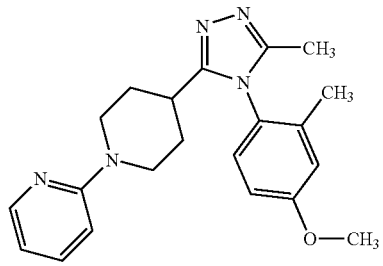

The oxadiazole of Preparation 6 (250 mg, 1.025 mmol) was combined with 4-methoxy-2-methylaniline (0.39 mL, 3.07 mmol), p-toluenesulphonic acid monohydrate (50 mg, 0.26 mmol), and xylene (3 mL). The mixture was heated to 150° C. with stirring for 18 hours. The solvent was then evaporated under reduced pressure, and then purified by flash chromatography on silica gel, eluting with ethyl acetate:methanol (90:10). The title compound was obtained as a colourless gum (257 mg) after trituration with diethyl ether.

$^1$H NMR (400 MHz, CD$_3$OD): δ 1.81 (m, 2H), 1.90 (m, 2H), 1.97 (s, 3H), 2.12 (s, 3H), 2.63 (m, 1H), 2.79 (m, 2H), 3.85 (s, 3H), 4.24 (m, 2H), 6.61 (m, 1H), 6.79 (d, 1H), 6.98 (m, 1H), 7.04 (s, 1H), 7.33 (d, 1H), 7.51 (m, 1H), 8.03 (m, 1H); LRMS: m/z ES$^+$ 364 [M+H$^+$

EXAMPLES 9 to 20

The compounds of the following tabulated examples of the general formula:

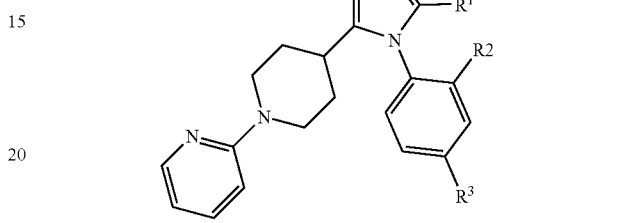

were prepared by a similar method to that of Example 8, as described in the footnotes to the table below, using the appropriate oxadiazole starting material and the corresponding anilines.

| Eg. | R$^1$ | R2 | R$^3$ | Analytical Data |
|---|---|---|---|---|
| 9[6] | CH$_3$ | CH$_3$ | Cl | $^1$HNMR (400MHz, CD$_3$OD): δ 1.82 (m, 2H), 1.96 (m, 2H), 2.01 (s, 3H), 2.14 (s, 3H), 2.63 (m, 1H), 2.78 (m, 2H), 4.25 (br m, 2H), 6.61 (m, 1H), 6.90 (d, 1H), 7.35 (d, 1H), 7.45 (m, 1H), 7.50 (m, 1H), 7.56 (m, 1H), 8.03 (m, 1H). LRMS m/z 368 [M + H]$^+$ |
| 10[7] | CH$_3$ | CH$_3$ | H | $^1$HNMR (400MHz, CD$_3$OD): δ 1.76-2.00 (m, 4H), 2.03 (s, 3H), 2.16 (s, 3H), 2.64 (m, 1H), 2.74 (m, 2H), 4.25 (m, 2H), 6.62 (t, 1H), 6.79 (d, 1H), 7.34 (d, 1H), 7.44-7.55 (m, 4H), 8.04 (d, 1H). LRMS m/z 334 [M + H]$^+$ |
| 11[7] | CH$_3$ | H | Cl | $^1$HNMR (400MHz, CD$_3$OD): δ 1.87 (m, 4H), 2.33 (s, 3H), 2.75-2.83 (m, 3H), 4.26 (m, 2H), 6.62 (t, 1H), 6.80 (d, 1H), 7.47 (d, 2H), 7.52 (t, 1H), 7.66 (d, 2H), 8.04 (d, 1H) LRMS m/z 354 [M + H]$^+$ |
| 12[7] | ![pyrazolylmethyl] | H | OCH$_3$ | $^1$HNMR (400MHz, CD$_3$OD): δ 1.87 (m, 4H), 2.76 (m, 3H), 3.85 (s, 3H), 4.25 (m, 2H), 5.65 (s, 2H), 6.62 (t, 1H), 6.79 (d, 1H), 7.02 (d, 2H), 7.15 (d, 2H), 7.51 (t, 1H), 7.59 (s, 2H), 8.03 (d, 1H). LRMS m/z 312 [M + H]$^+$ |
| 13[8] | CH$_3$ | H | OCH$_3$ | $^1$HNMR (400MHz, CD$_3$OD): δ 1.87 (m, 4H), 2.21 (s, 3H), 2.73-2.84 (m, 3H), 3.89 (s, 3H), 4.26 (m, 2H), 6.62 (t, 1H), 6.80 (d, 1H), 7.15 (d, 2H), 7.34 (d, 2H), 7.51 (t, 1H), 8.03 (d, 1H). LRMS m/z 350 [M + H]$^+$ |
| 14[8] | ![pyrazolylmethyl] | CH$_3$ | H | $^1$HNMR (400MHz, CD$_3$OD): δ 1.72-1.85 (m, 3H), 1.88 (s, 3H), 2.04 (m, 1H), 2.61 (m, 1H), 2.68-2.81 (m, 2H), 4.20-4.30 (m, 2H), 5.55-5.68 (m, 2H), 6.62 (t, 1H), 6.79 (d, 1H), 7.15 (d, 1H), 7.34 (t, 1H), 7.42 (m, 1H), 7.46-7.53 (m, 2H), 7.56 (s, 2H), 8.04 (d, 1H). LRMS m/z 401 [M + H]$^+$ |
| 15[8] | ![pyrazolylmethyl] | CH$_3$ | Cl | $^1$HNMR (400MHz, CD$_3$OD): δ 1.75-1.88 (m, 6H), 2.03 (m, 1H), 2.62 (m, 1H), 2.71-2.85 (m, 2H), 4.21-4.31 (m, 2H), 5.59-5.70 (m, 2H), 6.63 (t, 1H), 6.80 (d, 1H), 7.17 (d, 1H), 7.35 (d, 1H), 7.45 (s, 1H), 7.52 (t, 1H), 7.58 (s, 2H), 8.03 (d, 1H). LRMS m/z 435 [M + H]$^+$ |

-continued

| Eg. | R¹ | R2 | R³ | Analytical Data |
|---|---|---|---|---|
| 16[8] | (1,2,3-triazolylmethyl) | H | H | ¹HNMR (400MHz, CD$_3$OD): δ 1.88 (m, 4H), 2.71-2.83 (m, 3H), 4.25 (m, 2H), 5.67 (s, 2H), 6.62 (t, 1H), 6.79 (d, 1H), 7.25 (d, 2H), 7.49-7.56 (m, 6H), 8.03 (d, 1H). LRMS m/z 387 [M + H]$^+$ |
| 17[8] | (1,2,3-triazolylmethyl) | H | Cl | ¹HNMR (400MHz, CD$_3$OD): δ 1.87 (m, 4H), 2.74-2.83 (m, 3H), 4.25 (m, 2H), 5.69 (s, 2H), 6.62 (t, 1H), 6.80 (d, 1H), 7.26 (d, 2H), 7.51 (m, 3H),), 7.58 (s, 2H), 8.03 (d, 1H). LRMS m/z 421 [M + H]$^+$ |
| 18[9] | CH$_3$ | H | CH$_3$ | Retention time 0.30 minutes[16] |
| 19[9] | CH$_3$ | CH$_3$ | CH$_3$ | LRMS m/z ES$^+$ 373.99 [M + Na]$^+$ Retention time 0.30 minutes[10] |
| 20[11] | (morpholinylmethyl) | CH$_3$ | Cl | ¹HNMR (400MHz DMSO-d$_6$): δ 1.45-1.90 (m, 4H), 2.13 (m, 2H), 2.21 (m, 2H), 2.55 (m, 1H), 2.70-2.87 (m, 2H), 3.20-3.39 (m, 3H), 3.28 (s, 3H), 4.21 (m, 5H), 6.56 (m, 1H), 6.79 (m, 1H), 7.44 (m, 3H), 7.58 (s, 1H), 8.06 (m, 1H). LRMS m/z 453 [M + H]$^+$ |

[6]8 mL of xylene used and heated for 18 hours, then volume reduced to 3 mL and heated for a further 12 hours.
[7]2 mL of xylene used, 20 mg of p-toluene sulphonic acid, and 4 equivalents of aniline. After heating reaction mixture partitioned against dichloromethane and sodium hydrogen carbonate (aqueous saturated) before chromatography.
[8]3 mL of xylene used, 20 mg of p-toluene sulphonic acid, and 4 equivalents of aniline. After heating reaction mixture partitioned against dichloromethane and sodium hydrogen carbonate (aqueous saturated) before chromatography.
[9]4.9 mg (20 μmol) Oxadiazole starting material, 0.5 mg p-toluene sulphonic acid, 3 equivalents of aniline, and 0.2 mL of xylene heated to 120° C. in a sealed vessel for 24 hours. Purified by prep HPLC
[10]Purified using a Phenomenex C18 column eluting with aqueous (A): [trifluoroacetic acid in water (0.1% v/v): acetonitrile (95/5 v/v)]; organic(B): acetonitrile. Gradient 0-0.5 minutes 5% B; 0.5-0.6 minutes 5-10% B; 0.6-7.0 minutes 10-95%: 7.0-9.8 minutes 95%; 9.8-9.9 minutes 95-5%; 9.9-11 minutes 5%. Wavelength 225 nM; flow rate 8 mL/minute, ambient temperature
[11]4 equivalents of aniline used and no xylene.

All of the compounds exemplified above showed a Ki value of less than 400 nM when tested in screen 1.0 (V$_{1A}$ filter binding assay) as described above. Examples of specific compounds are illustrated in Table 2 below.

TABLE 2

| Example No. | Ki (nM) |
|---|---|
| 9 | 3.32 |
| 11 | 5.15 |
| 15 | 0.86 |
| 17 | 0.47 |

The invention claimed is:

1. A compound of formula (I), (I)

or a pharmaceutically acceptable salt thereof, wherein:
Het is 2-pyridinyl or 2-pyrimidinyl;
R¹ is H, C$_{1-3}$ alkyl or a nitrogen-containing heterocyclic ring having 5 or 6 ring atoms;
R² is H, benzyl or C$_{1-3}$ alkyl; and
R³ is H, methyl, methoxy or chloro.

2. The compound according to claim 1, or a pharmaceutically acceptable salt thereof, wherein Het is 2-pyridinyl.

3. The compound according to claim 1, or a pharmaceutically acceptable salt thereof, wherein R¹ is 1,2,3-triazolyl.

4. The compound according to claim 1, or a pharmaceutically acceptable salt thereof, wherein R² is H or methyl.

5. The compound according to claim 1, or a pharmaceutically acceptable salt thereof, wherein R³ is chloro.

6. The compound as claimed in claim 1, or a pharmaceutically acceptable salt thereof, wherein at least one of R¹, R² and R³ is a group other than H.

7. A compound as claimed in claim 1, or a pharmaceutically acceptable salt thereof, wherein R¹ is 1,2,3-triazolyl and R³ is chloro.

8.   2-{4-[4-(2-Ethyl-phenyl)-5-methyl-4H-[1,2,4]triazol-3-yl]-piperidin-1-yl}-pyrimidine;
2-{4-[5-Methyl-4-(2-propyl-phenyl)-4H-[1,2,4]triazol-3-yl]-piperidin-1-yl}-pyrimidine;
2-{4-[4-(2-Isopropyl-phenyl)-5-methyl-4H-[1,2,4]triazol-3-yl]-piperidin-1-yl}-pyrimidine
4-(5-Morpholin-4-ylmethyl-4-phenyl-4H-[1,2,4]triazol-3-yl)-3,4,5,6-tetrahydro-2H-[1,2']bipyridinyl;
4-(5-Butyl-4-phenyl-4H-[1,2,4]trizaol-3-yl)-3,4,5,6-tetrahydro-2H-[1,2']bipyridinyl;
4-(4-Phenyl-5-piperidin-1-ylmethyl-4H-[1,2,4]triazol-3-yl)-3,4,5,6-tetrahydro-2H-[1,2']bipyridinyl;

4-(5-Methyl-4-phenyl-4H-[1,2,4]triazol-3-yl)-3,4,5,6-tetrahydro-2H-[1,2']bipyridinyl;

4-[4-(4-Methoxy-2methyl-phenyl)-5-methyl-4H-[1,2,4]triazol-3-yl]-3,4,5,6-tetrahydro-2H-[1,2']bipyridinyl;

4-[4-(4-Chloro-2methyl-phenyl)-5-methyl-4H-[1,2,4]triazol-3-yl]-3,4,5,6-tetrahydro-2H-[1,2,']bipyridinyl;

4-(5-Methyl-4-o-tolyl-4H-[1,2,4]triazol-3-yl)-3,4,5,6-tetrahydro-2H-[1,2']bipyridinyl;

4-[4-(4Chloro-phenyl)-5-methyl-4H-[1,2,4]triazol-3-yl]-3,4,5,6-tetrahydro-2H-[1,2']bipyridinyl;

4-[4-(4-Methoxy-phenyl)-5-[1,2,3]triazol-2-ylmethyl-4H-[1,2,4]triazol-3-yl]-3,4,5,6-tetrahydro-2H-[1,2']bipyridinyl;

4-[4-(4-Methoxy-phenyl)-5-methyl-4H-1,2,4]triazol-3-yl]-3,4,5,6-tetrahydro-2H-1,2']bipyridinyl;

4-(4-o-Tolyl-5-[1,2,3]triazol-2-ylmethyl-4H-1,2,4]triazol-3-yl)-3,4,5,6-tetrahydro-2H-[1,2']bipyridinyl;

4-[4-(4-Chloro-2-methyl-phenyl)-5-[1,2,3]triazol-2-ylmethyl-4H-[1,2,4]triazol-3-yl]-3,4,5,6-tetrahydro-2H-[1,2']bipyridinyl;

4-(4-Phenyl-5-[1,2,3]triazol-2-ylmethyl-4H-[1,2,4]triazol-3-yl)-3,4,5,6-tetrahydro-2H-[1,2']bipyridinyl;

4-[4-(4-Chloro-phenyl)-5-[1,2,3]triazol-2-ylmethyl-4H-[1,2,4]triazol-3,4,5,6-tetrahydro-2H-[1,2']bipyridinyl;

4-(5-Methyl-4-p-toyl-4H-[1,2,4]triazol-3-yl)-3,4,5,6-tetrahydro-2H-[1,2']bipyridinyl;

4-[4-(2,4-Dimethyl-phenyl)-5-methyl-4H-[1,2,4]triazol-3-yl]-3,4,5,6-tetrahydro-2H-[1,2']bipyridinyl; or 4-[4-(4-Chloro-2-methyl-phenyl)-5-morpholin-4-ylmethyl-4H-[1,2,4]triazol-3-yl]-3,4,5,6-tetrahydro-2H-[1,2']bipyridinyl;

or a pharmaceutically acceptable salt thereof.

9. A method of treating a disorder selected from primary dysmennorhea, secondary dysmennorhea, premature ejaculation, or rheumatoid arthritis comprising administering a therapeutically effective amount of a compound according to claim 1, or a pharmaceutically acceptable salt thereof, to a patient suffering from such a disorder.

10. The method according to claim 9 wherein the disorder is primary dysmennorhea or secondary dysmennorhea.

11. The method according to claim 10 wherein the disorder is primary dysmennorhea.

12. A pharmaceutical composition comprising a compound according to claim 1 or a pharmaceutically acceptable salt thereof, together with a pharmaceutically acceptable excipient, diluent or carrier.

13. A pharmaceutical composition comprising a compound according to claim 1 or a pharmaceutically acceptable salt thereof in combination with a compound selected from (a) an oral contraceptive, (b) a PDE5 inhibitor, (c) an NO donor, (d) L-arginine, or (e) a COX inhibitor, together with a pharmaceutically acceptable acceptable excipient, carrier or diluent.

* * * * *